United States Patent
Noguchi et al.

(10) Patent No.: US 10,251,988 B2
(45) Date of Patent: *Apr. 9, 2019

(54) DIALYSIS AGENT A CONTAINING ACETIC ACID AND ACETATE SALT, AND A TWO-PART DIALYSIS AGENT USING THEREOF

(71) Applicant: Tomita Pharmaceutical Co., Ltd., Naruto-shi, Tokushima (JP)

(72) Inventors: Hiroshi Noguchi, Naruto (JP); Michiko Myose, Naruto (JP); Junya Kikuishi, Naruto (JP); Mina Hashimoto, Naruto (JP); Hideyuki Aoyama, Naruto (JP)

(73) Assignee: Tomita Pharmaceutical Co., Ltd., Naruto-shi, Tokushima (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/900,162

(22) Filed: Feb. 20, 2018

(65) Prior Publication Data
US 2018/0169317 A1    Jun. 21, 2018

Related U.S. Application Data

(63) Continuation of application No. 14/049,644, filed on Oct. 9, 2013, now Pat. No. 9,931,453.

(30) Foreign Application Priority Data

Oct. 10, 2012 (JP) .................. 2012-225060
Feb. 4, 2013 (JP) .................. 2013-019737

(51) Int. Cl.
| | |
|---|---|
| *A61M 1/16* | (2006.01) |
| *A61K 33/14* | (2006.01) |
| *A61K 31/19* | (2006.01) |
| *A61K 31/191* | (2006.01) |
| *A61K 31/194* | (2006.01) |
| *A61K 31/7004* | (2006.01) |
| *A61K 33/06* | (2006.01) |
| *A61K 33/10* | (2006.01) |

(52) U.S. Cl.
CPC .......... *A61M 1/1654* (2013.01); *A61K 31/19* (2013.01); *A61K 31/191* (2013.01); *A61K 31/194* (2013.01); *A61K 31/7004* (2013.01); *A61K 33/06* (2013.01); *A61K 33/10* (2013.01); *A61K 33/14* (2013.01)

(58) Field of Classification Search
CPC .................................................. A61M 1/1654
See application file for complete search history.

(56) References Cited

U.S. PATENT DOCUMENTS

| | | | | |
|---|---|---|---|---|
| 4,655,941 A * | 4/1987 | Suzuki | .................. | A61K 9/14 159/48.1 |
| 4,756,838 A * | 7/1988 | Veltman | .............. | A61M 1/1654 210/646 |
| 5,091,094 A * | 2/1992 | Veech | ................. | A61M 1/1656 210/321.71 |
| 5,122,516 A * | 6/1992 | Watanabe | ........... | A61M 1/1654 210/646 |
| 5,252,213 A * | 10/1993 | Ahmad | ................. | A61M 1/169 210/542 |
| 5,318,750 A * | 6/1994 | Lascombes | ............. | A61J 3/002 137/268 |
| 5,540,842 A * | 7/1996 | Aoyama | .............. | A61K 9/1688 210/542 |
| 5,616,248 A * | 4/1997 | Schal | ..................... | A61K 33/14 210/646 |
| 6,309,673 B1 * | 10/2001 | Duponchelle | .......... | A61K 33/14 424/677 |
| 6,399,110 B1 | 6/2002 | Kikuchi et al. | | |
| 6,399,310 B1 * | 6/2002 | Murphy, Jr. | ......... | C12Q 1/6883 435/6.16 |
| 6,428,706 B1 * | 8/2002 | Rosenqvist | ......... | A61M 1/1656 210/232 |
| 6,475,529 B2 * | 11/2002 | Duponchelle | .......... | A61K 33/14 206/219 |
| 2004/0060865 A1 * | 4/2004 | Callan | .................... | A61K 31/19 210/646 |
| 2007/0231395 A1 * | 10/2007 | Kai | ...................... | A61K 9/0095 424/490 |
| 2013/0168316 A1 * | 7/2013 | Noguchi | ............. | A61M 1/1656 210/647 |
| 2013/0189376 A1 * | 7/2013 | Carlsson | .............. | A61K 9/0029 424/678 |
| 2014/0097386 A1 * | 4/2014 | Noguchi | ............ | A61K 31/7004 252/364 |

FOREIGN PATENT DOCUMENTS

| | | | | |
|---|---|---|---|---|
| CA | -2301577 A1 * | 3/1999 | ............. | A61K 45/06 |
| CN | 1448145 A | 10/2003 | | |
| CN | 1744884 A | 3/2006 | | |
| EP | 0597817 A2 | 5/1994 | | |
| JP | H06-245995 A | 9/1994 | | |
| JP | H07-024061 A | 1/1995 | | |
| JP | H07-059846 A | 3/1995 | | |
| JP | H10-087478 | 4/1998 | | |
| JP | H10-259133 A | 9/1998 | | |
| JP | 2003-104869 A | 4/2003 | | |
| JP | 2007-130165 A | 5/2007 | | |
| JP | 4603977 B2 | 12/2010 | | |
| JP | 2013-150767 A | 8/2013 | | |
| JP | 2014-094928 A | 5/2014 | | |
| JP | 5517322 B1 | 6/2014 | | |
| WO | WO 94/16663 | 8/1994 | | |
| WO | WO 99/09953 A1 | 3/1999 | | |
| WO | WO 2004/066977 A1 | 8/2004 | | |
| WO | WO 2005/094918 A1 | 10/2005 | | |
| WO | WO 2010/112570 A1 | 10/2010 | | |

* cited by examiner

*Primary Examiner* — Nicole M. Buie-Hatcher
*Assistant Examiner* — M. Reza Asdjodi
(74) *Attorney, Agent, or Firm* — Knobbe, Martens, Olson & Bear, LLP

(57) ABSTRACT

A dialysis agent A including a mixture containing glucose, acetic acid, and acetate salt, but not sodium bicarbonate, wherein the molar ratio of acetic acid:acetate salt is 1:0.5 to 1:2, and wherein a total amount of the acetic acid and acetate salt contained in the dialysis agent A is between 2 mEq/L and 6 mEq/L when the dialysis agent A is dissolved in 1 L of a bicarbonate dialysate.

17 Claims, No Drawings

DIALYSIS AGENT A CONTAINING ACETIC ACID AND ACETATE SALT, AND A TWO-PART DIALYSIS AGENT USING THEREOF

BACKGROUND OF THE INVENTION (1) Field of the Invention

The present invention relates to a dialysis agent A used as a two pack type dialysis agent containing acetic acid and acetate salt. More specifically, the present invention relates to a dialysis agent A used to prepare a bicarbonate dialysate together with a dialysis agent B containing sodium hydrogen carbonate, that can adjust the total acetate ion concentration in the dialysate to less than 6 mEq/L and is excellent in the storage stability of glucose and the like, as well as able to reduce the acetic acid odor and suppress the corrosion of the dialysate delivery system and the dialysis machine. Furthermore, the present invention relates to a two pack type dialysis agent containing the dialysis agent A.

(2) Description of Related Art

Dialysis therapy has been established as a treatment for patients with renal insufficiency, and performed for the purpose of controlling the concentration of blood electrolyte components, removal of uremic substances, correction of acid-base balance, or the like. Although a plurality of components are included in the dialysis solution used in the dialysis treatment, the components satisfying the objectives of treatment and with less burden on the living body should be combined at appropriate concentrations.

In recent years, a bicarbonate dialysate using sodium hydrogen carbonate for the correction of acid-base balance has become the mainstream in the hemodialysis solution, and it is also essential to combine an acid to make the dialysate neutral. Further, when these are distributed in the same container in which they coexist, such components generate carbon dioxide gas in the container, so that they become very unstable, because of which two agents separated into agent A and agent B as a dialysis agent used for the preparation of the dialysate are generally mixed at the time of use.

Usually, the agent A contains sodium chloride, potassium chloride, calcium chloride, magnesium chloride, pH adjusting agent (acid and buffer components as optional components), and glucose, and the agent B contains sodium hydrogen carbonate. Moreover, in order to prevent the precipitation of insoluble salts, it is said that the formulation of calcium chloride and magnesium chloride into the agent B is contraindicated.

Conventionally, these agents A and B have been used as a liquid filled in a polyethylene container, but transportation costs and poor workability in hospitals (weight, storage space, and disposal method of polyethylene container) have become a problem. As a result, today, a dialysis agent in powder form to be mixed with water before use has been put into practical use.

Although the dialysis agent in powder form was originally comprised of three agents including an agent A-1 containing a pH adjusting agent and an electrolyte, an A-2 agent consisting of only glucose, and an agent B consisting of sodium hydrogen carbonate, but currently the agent A-1 and the agent A-2 are combined to form a two pack type consisting of the agent A and the agent B, said two pack type being the mainstream.

Today, the bicarbonate dialysis agent is formulated so as to have the following composition and concentration when clinically used as a dialysate.

TABLE 1

| | |
|---|---|
| $Na^+$: | 130 to 150 mEq/L |
| $K^+$: | 0 to 3.0 mEq/L |
| $Ca^{2+}$: | 2.0 to 4.0 mEq/L |
| $Mg^{2+}$: | 0 to 2.0 mEq/L |
| $Cl^-$: | 90 to 120 mEq/L |
| $HCO_3^-$: | 20 to 40 mEq/L |
| Acetic acid: | 0 to 12 mEq/L |
| Citric acid: | 0 to 3 mEq/L |
| Glucose: | 0 to 250 mg/dL |

The dialysate at the time of dialysis treatment is used by diluting and mixing a liquid type agent A, or the agent A obtained by dissolving a powder type agent A, or the agent A obtained by dissolving a powder type agent A-1 or A-2, with a liquid type agent B, or the agent B obtained by dissolving a powder type agent B. However, as mentioned above, carbon dioxide gas is generated as a result of coexistence of an acid and sodium hydrogen carbonate over time and the pH rises at the same time, so that an insoluble calcium carbonate and the like may be generated. By this phenomenon, there has been raised such a problem that calcium concentration effective in the treatment is reduced and crystals are adhered to the tube or hose of the dialysis device.

On the other hand, acetic acid has been used for a long time as a pH adjusting agent, but, in recent years, peripheral vasodilator action and cardiac inhibitory effect, induction of inflammatory cytokines, and burden on the patient with acetate intolerance, due to acetic acid have been questioned. That is, because acetic acid is metabolized in a short time, it is not accumulated in the living body, but it has a cardiac inhibitory effect, a peripheral vasodilator action, and, as a result, an action of reducing blood pressure. Because dialysis treatment is also a treatment for the removal of moisture in the body, a reduction in blood pressure due to moisture removal during dialysis and after dialysis would inevitably occur. The symptomatic treatment such as control of moisture removal and administration of vasopressors is often used in combination to prevent the reduction in blood pressure. The presence or absence of symptoms caused by these effects are different for each patient, and thus it is thought that such symptoms may also be attributed to the concentration of acetic acid contained in the dialysate. In recent years, a dialysis method without acetic acid (an acetate free dialysis method) as one approach to overcome such a situation has been proposed.

Therefore, nowadays, those obtained by formulating citric acid in place of acetic acid as a pH adjusting agent are commercially available and have been clinically used (for example, see JP 2003-104869 A, WO 2005/094918, JP H10-087478 A and WO 2010/112570). However, there has been raised such a problem that because citric acid has a strong chelating action, a portion of the calcium in the dialysate is chelated, thereby to decrease the ionized calcium concentration, and because citric acid is a stronger acid than acetic acid, the pH of the concentrated solution A becomes lower to cause a risk of corrosion of parts of a dialysate delivery system or a dialysis machine. On the contrary, if a large amount of organic acid salts are formulated in order to increase the pH of the solution A, crystals of calcium citrate are precipitated to affect the composition, and this is also a problem. In other words, because citric acid is easy to form a chelate with an alkaline earth metal, it forms a chelate with calcium and magnesium in the dialysate component. This effect is stronger for calcium in particular, and since control of the amount of calcium is very important in dialysis treatment, there is a drawback such that decrease of ionized calcium concentration due to such a chelate significantly affects the calcium balance in patients. For example, if the calcium and citric acid were included at almost the same concentration (ion equivalent ratio) in the dialysate, about 35% of calcium is chelated to reduce the ionized calcium concentration in the dialysate by a corresponding amount, resulting in a difficulty to control the blood calcium level. In addition, since citric acid also enters the body by dialysis, there is a risk such that citric acid binds to calcium in the blood to generate a poorly soluble calcium citrate, which is then deposited in the blood vessel. In addition, there is a concern such that it becomes difficult to control the calcium important in the living body in dialysis patients because there is no explicit dynamics of the components such as citric acid and calcium after they entered the blood at the same time. Furthermore, there is a problem in the following points in that the decrease in ionized calcium concentration due to citric acid promotes the relaxation of cardiac muscle and vascular smooth muscle, leading to low blood pressure, and that citric acid is difficult to use in patients with bleeding tendency because it has an anticoagulant effect.

Further, citric acid is easy to handle in the normal handling because it is a solid, but since its concentrate is strongly acidic, hydrogen chloride gas is easily generated upon partial moisture absorption even if it is stored in powder form, which may cause a partial metal corrosion of the dialysate delivery system, resin deterioration, and the like. For example, JP 2003-104869 A describes a powder-type dialysis agent free from acetic acid, said dialysis agent being able to prevent the formation of insoluble compounds, suppress the precipitation of calcium carbonate, and inhibit the degradation of glucose by using a citric acid. These effects can be achieved by using citric acid within a limited range of pH 2.2 to 2.9. There is a problem such that there is a risk of corrosion of the dialysate delivery system and the dialysis machine within such a pH range and the decrease in the ionized calcium concentration due to the strong chelation effect of citric acid may also affect the therapeutic effect as described above.

Therefore, it is not optimal to use citric acid as an acid other than acetic acid and it is considered to use safe substances to the living body, such as an organic acid other than citric acid, including lactic acid, malic acid, fumaric acid, gluconic acid, etc., but it is also important to reduce the amount of these acids as much as possible because it is not clear about their behavior in the body after dialysis in chronic use and to take into account the influence of these acid components on the dialysate delivery system and the dialysis machine.

On the other hand, as described above, citric acid etc. would decrease the ionized calcium concentration due to its strong chelating action is concerned, but, strictly speaking, acetic acid also reduces the ionized calcium concentration. The clinical problem of acetic acid has been neglected because of its probable faster metabolism, but, in practice, the ionized calcium concentration when formed into a dialysate using acetic acid becomes lower than that of a dialysate using hydrochloric acid as the pH adjusting agent, and the ionized calcium concentration is further reduced as the content of acetic acid is increased. Although not known in general, it is certain that a large content of acetic acid becomes a factor in lowering the ionized calcium concentration, but not as much as citric acid, in the dialysis. From this point, it is clear that a less content of acetic acid is desirable.

The dialysis agent A containing acetic acid, which has been sold in Japan in the past, has a total acetic acid content of 8 mEq/L or more and a ratio of 1:2.2 or more of acetic acid:sodium acetate regardless of a liquid or a solid. The dialysis agent A having the ratio less than the above has not been used. Since the pH of the liquid A is 4.6 or more under this condition, there is such an advantage that the dialysate delivery system is less likely to be corroded and easy to handle, when viewed from the aspect of production of the liquid formulation.

The reason of the formulation of 8 mEq/L or more of the total acetate content in Japan is because benefits of bicarbonate and benefits of acetate, i.e., benefits to correct blood bicarbonate ions directly and benefits to correct bicarbonate ions slowly through the acetate metabolism are combined so as to obtain a dual formulation when changed to the bicarbonate dialysis agent from the past acetate dialysis agent (sodium acetate is formulated in 30 mEq/L or more without using sodium bicarbonate).

On the other hand, liquid preparations (liquid A) are sold primarily outside of Japan. Since in Japan, sodium acetate is used as a part of the alkalizing agent, but only sodium bicarbonate as the agent B is used as the alkalizing agent outside of Japan, sodium acetate has not been used. Therefore, as an acetate component, only acetic acid in an amount of 4 mEq/L or less has been used mainly as a pH adjusting agent.

However, when sodium acetate is not included as described above, the pH of liquid A becomes 3 or less, resulting in adverse effects such as corrosion of the metal member of the dialysate delivery system and the dialysis machine, and strong irritation to the skin. In late years, a liquid A (including those that were prepared by dissolving an agent A powder) having a pH of 3 or less has been commercially available and the dialysate preparation equipment manufacturers also deal with such a liquid A by employing acid resistant materials strongly resistant to corrosion as a component material. However, these materials are economically unfavorable because they are expensive.

In addition, the dialysate containing acetic acid in the dialysis facilities where large quantities of acetic acid are handled even though it is a liquid, and acetic acid odor is very strong and uncomfortable, because of which it also becomes necessary to care the dialysis agent not to be placed in an open system as much as possible during its manufacturing or handling.

Next, in Japan, powder preparations of dialysis agents become the mainstream from the flow of powdering, and a number of patents relating to bicarbonate dialysis agents corresponding to such powdering have been disclosed. For example, JP H07-24061 A describes that the manufacturing of the powder preparation becomes easier, when sodium acetate is combined to acetic acid in a ratio (molar ratio) of 1.56 to 3.29, preferably 2.49 to 3.29, in a powdery dialysis agent A because sodium acetate easily adsorbs acetic acid and is difficult to volatilize. However, even in the technique disclosed by JP H07-24061 A, the total acetate ion content of the finally prepared dialysate is assumed to be 8 mEq/L or more.

In addition, it is typical that sodium acetate is combined in an amount of from more than two times to five times, relative to acetic acid, and, for example, combination ratio of sodium acetate is 2.2 times (acetic acid 2.5 mEq/L: sodium acetate 5.5 mEq/L) for commercially available LYMPACK TA-1 in Japan, three times (acetic acid 2 mEq/L:sodium acetate 6 mEq/L) for KINDALY 2E, 4.5 times (acetic acid 2 mEq/L:sodium acetate 9 mEq/L) for HYSORB-F, and 5 times (acetic acid 2 mEq/L:sodium acetate 10 mEq/L) for HYSORB-D. Even apart from the transition of formulation in the past, the reason why the ratio of two times or less of sodium acetate to acetic acid has not yet been disclosed is because there was a problem with acetic acid odor. In other words, as the ratio of sodium acetate is increased to three times and four times, the acetic acid odor in powder preparation is reduced. On the contrary, the ratio of sodium acetate relative to acetic acid becomes close to double or becomes double or less, an excruciating acetic acid odor occurs, because of which its practical use is not possible.

As seen from the above, even in Japan and abroad, there remains use of a dialysate using acetic acid and having a total acetate ion content of 4 mEq/L or less, or 8 mEq/L or more, and there has been no dialysis agent put to practical use, wherein the pH of the liquid A (concentrate) obtained by dissolving a solid agent A in water is set to about 4 and the total acetate ion content in the dialysate is set to 4 to 8 mEq/L.

Only JP H06-245995 A discloses that a preferable total acetate ion content is up to 5 mEq/L in the dialysate using acetic acid and sodium acetate. However, JP H06-245995 A discloses a primary concentrate (sodium hydrogen carbonate, sodium chloride, and sodium acetate) and an individual concentrate (sodium, potassium, calcium, magnesium, hydrochloric acid/or acetic acid, glucose), and describes that the molar ratio of acetate/sodium in the final dialysate obtained by combining the primary concentrate with the individual concentrate is 0.03 or less. That is, if the sodium content in the dialysate is typically set to 140 mEq/L, the total content of acetate ions in the dialysate corresponds to 4.2 mEq/L or less. Further, the sodium acetate to be combined with the primary concentrate is in an acetate/sodium ratio of less than 0.03, and this indicates that the acetate ion content in the dialysate is less than about 4 mEq/L. That is, JP H06-245995 A discloses the embodiment of only a dialysis agent useful in the production of a dialysate having a total acetate ion content of less than about 4 mEq/L.

In addition, the dialysis agent of JP H06-245995 A enables individual patients to select various individual concentrates that can be provided, and the object of combining sodium acetate is to improve the stability and preserving property of the primary concentrate at low temperatures. In other words, a small amount of sodium acetate in the primary concentrate increases the solubility of sodium hydrogen carbonate and suppresses the formation of precipitates.

That is, since the dialysis agent of JP H06-245995 A enables to perform the dialysis with various formulations according to the individual patients (calcium, magnesium, potassium, etc.) and requires a fairly complex system so that acetic acid and acetate salt are designed to be combined into different preparations respectively, it differs from a two pack type dialysis agent comprising generally agent A and agent B in its dosage form and preparation method of the dialysate. In addition, the technical means for reducing the acetic acid odor in the dialysis agent has not been studied at all in JP H06-245995 A. Further, in the dialysis agent of JP H06-245995 A, since the individual concentrate includes hydrochloric acid or acetic acid and does not include a basic component, so that it will be exposed to a strong acidic condition of pH 3 or less, it cannot be said that the dialysis agent of JP H06-245995 A is not necessarily a good preparation in regard to corrosion problems of the dialysate delivery system, stability of glucose, and the like.

As described above, in combination of the agent A (electrolytes, acids, glucose, etc.) and the agent B (sodium hydrogen carbonate) that is widely used as a general two pack type dialysis agent, a dialysis agent having a total acetate ion content of 4 to 8 mEq/L does not exist, let alone there was no dialysis agent in powder form for practical use due to its strong acetic acid odor.

In fact, domestically and abroad, there is no successful example of any actual commercialization of dialysis agents in powder form, wherein the total acetate ion content has been set to less than 8 mEq/L in the dialysate. This is probably because commercialization capable of withstanding clinical use in terms of fluidity and stability, and acetic acid odor as a dialysis agent in powder form is difficult. For example, acetic acid has a big influence on environment in the point with its pungent odor. Clinical dialysate preparation is generally performed by a clinical engineer, but there is a problem at the point of discomfort associated with pungent odor that is generated. Furthermore, because acetic acid also becomes the degradation factor of glucose, a formulation design with sufficient consideration of stability of glucose is required for a dialysis agent using acetic acid and containing glucose. Therefore, it is necessary to find the optimal formulation while sufficiently considering such problems.

In recent years, it has been reported at conferences and the like that a lower content of total acetate ions in the dialysate is physiologically desirable and the total acetate ions are preferably less than 6 mEq/L or less than 4 mEq/L. Thus, development of a dialysis agent that can be set to a lower total acetate ion content has been more and more strongly demanded. By suppressing the total acetate ion content within a low range in this way, it is believed that the onset of symptoms such as decrease in blood pressure can be suppressed without almost raising blood acetic acid concentration of the patient during dialysis, thereby to significantly improve safety, because the metabolic rate of acetic acid is faster than that of other organic acids and the content of acetic acid is less than that of conventional products.

Based on the background of such a prior art, the development of a dialysis agent that is able to set the total acetate ion content in the dialysate to a low value, is excellent in storage stability of glucose or the like, can reduce the acetic acid odor and suppress the corrosion of the dialysate delivery system and the dialysis machine, and can be put into practical use, has been desired.

SUMMARY OF THE INVENTION

An object of the present invention is to provide a dialysis agent A that is able to set the total acetate ion content in the dialysate to a low value, is excellent in storage stability of glucose or the like, and can reduce the acetic acid odor and suppress the corrosion of the dialysate delivery system and the dialysis machine, as well as to provide a two pack type dialysis agent utilizing the dialysis agent A.

As a result of intensive studies to solve the above problems, the present inventors have found that in the dialysis agent A used in the preparation of a bicarbonate dialysate, which is used as one part of a two pack type dialysis agent, by including acetic acid and acetate salt together with glucose while allowing to satisfy a molar ratio of 1:0.5 to 2 of acetic acid:acetate salt, and including acetic acid and acetate salt in a total amount of between 2 mEq or more and less than 6 mEq in the dialysis agent A required to prepare 1 L of the bicarbonate dialysate, it becomes possible to prepare the bicarbonate dialysate having a total acetate ion concentration of between 2 mEq/L or more and less than 6 mEq/L so that in addition to the excellent stability of the components such as glucose and the like in the dialysis agent A, the acetic acid odor can be reduced and the corrosion of the dialysate delivery system and the dialysis machine can be suppressed. The present invention was completed by further studies on the basis of these findings.

That is, the present invention provides the invention with the following embodiments.

Item 1. A dialysis agent A used in the preparation of a bicarbonate dialysate, which is used as one part of a two pack type dialysis agent, comprising glucose, acetic acid, and acetate salt,
wherein the molar ratio of acetic acid:acetate salt is 1:0.5 to 2, and
acetic acid and acetate salt in a total amount of between 2 mEq or more and less than 6 mEq are contained in the dialysis agent A required to prepare 1 L of the bicarbonate dialysate.

Item 2. The dialysis agent A according to Item 1, wherein when the dialysis agent A is converted into a state of an aqueous solution that is concentrated to 35 times the concentration of each component in the finally prepared dialysate, the pH shows 3.9 to 4.6.

Item 3. The dialysis agent A according to Item 1 or 2, wherein the acetate salt is sodium acetate.

Item 4. The dialysis agent A according to any one of Items 1 to 3, which further comprises a physiologically available electrolyte other than acetic acid and acetate salt.

Item 5. The dialysis agent A according to Item 4, wherein the electrolyte comprises sodium chloride, potassium chloride, magnesium chloride, and calcium chloride.

Item 6. The dialysis agent A according to any one of Items 1 to 5, which is in the form of a solid.

Item 7. The dialysis agent A according to Item 6, wherein the acetic acid and acetate salt are contained as a mixture of acetic acid and acetate salt.

Item 8. The dialysis agent A according to Item 6 or 7, wherein the acetic acid and acetate salt are contained as a mixture of glacial acetic acid and anhydrous sodium acetate.

Item 9. The dialysis agent A according to any one of Items 6 to 8, comprising a first material consisting of a mixture of acetic acid and acetate salt and a second material consisting of a composition containing a physiologically available electrolyte other than acetic acid and acetate salt,
wherein all of the acetate salt in the dialysis agent A are contained in the first material, or some of the acetate salt in the dialysis agent A are also contained in the second material, and
glucose is contained in the composition of the second material, and/or
a third material containing glucose separately from the first material and the second material is contained.

Item 10. The dialysis agent A according to Item 9, wherein the second material contains sodium chloride, potassium chloride, magnesium chloride, and calcium chloride as an electrolyte.

Item 11. The dialysis agent A according to Item 9 or 10, wherein the second material further contains as an electrolyte an organic acid salt other than acetate salt.

Item 12. The dialysis agent A according to Item 11, wherein the organic acid salt is at least one kind selected from the group consisting of sodium lactate, sodium gluconate, sodium citrate, sodium malate, and sodium succinate.

Item 13. The dialysis agent A according to any one of Items 6 to 12, wherein the moisture content is 1.0% by weight or less.

Item 14. The dialysis agent A according to any one of Items 6 to 13, which is accommodated in a packaging container of a water vapor transmission of 0.5 $g/m^2 \cdot 24$ h or less.

Item 15. The dialysis agent A according to any one of Items 6 to 14, which is accommodated in a packaging container together with a desiccant.

Item 16. A two pack type dialysis agent comprising the dialysis agent A according to any one of Items 1 to 15 and a dialysis agent B containing sodium hydrogen carbonate.

Item 17. A method for preparing a bicarbonate dialysate, comprising the step of mixing the dialysis agent A according to any one of Items 1 to 15 and a dialysis agent B containing sodium hydrogen carbonate with water in an amount so as to have the total acetate ions of between 2 mEq/L or more and less than 6 mEq/L.

Item 18. A bicarbonate dialysate comprising glucose, acetic acid, and acetate salt, wherein the molar ratio of acetic acid:acetate salt is 1:0.5 to 2 and the total acetate ions are between 2 mEq/L or more and less than 6 mEq/L.

Since the dialysis agent A of the present invention is able to prepare a bicarbonate dialysate so as to have a total acetate ion concentration of less than 6 mEq/L, it is possible to suppress the onset of symptoms such as hypotension and the like and improve safety significantly during dialysis, as well as to effectively suppress the reduction of ionized calcium concentration in the dialysate. In addition, the dialysis agent A of the present invention is able to improve stability of components such as glucose and the like, reduce the acetic acid odor, and suppress the corrosion of the dialysate delivery system and the dialysis machine so that the quality is improved and the improvement of the usage environment is achieved in the medical settings, resulting in a marked improvement of handling in the medical settings.

Especially, in the dialysis agent A of the present invention, the pH of the liquid A (concentrate) obtained by dissolving a solid agent A in water or the pH of a liquid agent A can be adjusted to about 4.3 by setting the total acetate ion concentration in the dialysate so as to have 3 to 5 mEq/L and by setting the molar ratio of acetic acid:acetate salt to 1:1 to 1.5, so that a bicarbonate dialysis agent that is clinically more safer and more excellent in the stability of production and quality can be provided.

Thus, according to the present invention, the bicarbonate dialysate can be prepared so as to have a total acetate ion concentration of less than 6 mEq/L, and a dialysis agent A that is clinically more useful and more excellent in the storage property and handling property than the conventional solid or liquid dialysis agent A can be provided.

In addition, according to the present invention, by providing a two pack type dialysis agent in combination with the dialysis agent A and a dialysis agent B containing sodium hydrogen carbonate, it becomes possible to prepare a bicarbonate dialysate so as to have a total acetate ion concentration of less than 6 mEq/L with excellent safety, quality, and operability without adversely affecting the dialysate delivery system and the dialysis machine.

DETAILED DESCRIPTION OF PREFERRED EMBODIMENTS

As used herein, the indication "to" showing the numerical range means that it is equal to or more than the number at the left side and equal to or less than the number at the right side, and, for example, the numerical range of "X to Y" means "equal to or more than X and equal to or less than Y".

1. Dialysis Agent A

The dialysis agent A of the present invention is an agent A used in the preparation of a bicarbonate dialysate, which is used as one part of a two pack type dialysis agent, comprising glucose, acetic acid, and acetate salt, wherein the molar ratio of acetic acid:acetate salt is 1:0.5 to 2, and acetic acid and acetate salt in a total amount of between 2 mEq or more and less than 6 mEq are contained in the dialysis agent A required to prepare 1 L of the bicarbonate dialysate. The dialysis agent A of the present invention will be described in detail below.

<Acetic Acid and Acetate Salt>

The dialysis agent A of the present invention includes acetic acid and acetate salt. The acetic acid used in the present invention may be glacial acetic acid. Further, the acetate salt used in the present invention includes, for example, but not particularly limited to, sodium acetate, potassium acetate, calcium acetate, magnesium acetate, and the like, as long as it is acceptable as a component of dialysate. Among these acetate salts, sodium acetate is preferable from the viewpoint of safety as a result of use for many years and cost. Further, such acetate salts may be used alone or in combination of two or more kinds thereof. Incidentally, acetate salt may be anhydrous acetate salt.

The dialysis agent A of the present invention contains acetic acid and acetate salt so as to satisfy a molar ratio of acetic acid:acetate salt of 1:0.5 to 2. By satisfying such molar ratio, it becomes possible to allow the dialysate to have an appropriate pH due to the buffering action of acetic acid-acetate salt even if the total acetate ion concentration in the dialysate is set to less than 6 mEq/L. Further, by satisfying such molar ratio, it is possible to adjust the pH of the liquid A (concentrate) obtained by dissolving a solid agent A in water or the pH of the liquid agent A to about 3.9 to 4.6 so that it becomes possible to suppress the corrosion of the dialysate delivery system and the dialysis machine. Furthermore, by satisfying such molar ratio, it becomes possible to suppress the degradation of glucose and increase the storage stability of the dialysis agent A, and further possible to reduce the acetic acid odor.

As the ratio of acetic acid and acetate salt in the dialysis agent A of the present invention, the molar ratio of acetic acid and acetate salt is preferably 1:0.75 to 1.75, more preferably 1:0.75 to 1.5, even more preferably 1:1 to 1.5, and especially preferably 1:1 to 1.25, from the view point of exerting actions more effectively, including improvement of the stability of glucose, reduction of acetic acid odor, suppression of the corrosion of the dialysate delivery system and the dialysis machine, and the like.

For the content of acetic acid and acetate salt in the dialysis agent A of the present invention, it may be appropriately determined depending on whether the agent A is solid or liquid, but is usually set so as to satisfy a total acetate ion content in the finally prepared dialysate, of between 2 mEq/L or more and less than 6 mEq/L, preferably between 2 mEq/L or more and 5.5 mEq/L or less, and more preferably between 3 mEq/L or more and 5 mEq/L or less. That is, in the dialysis agent A of the present invention, the total amount of acetic acid and acetate salt is set to be between 2 mEq or more and less than 6 mEq, preferably between 2 mEq or more and 5.5 mEq or less, and more preferably between 3 mEq or more and 5 mEq or less, per the amount required to prepare 1 L of the bicarbonate dialysate. Thus, according to the dialysis agent A of the present invention, since it is possible to set the total acetate ion content in the dialysate to a lower level that has not been realized in the conventional two pack type dialysis agent, onset of symptoms such as hypotension induced by acetate ions during dialysis can be suppressed, thereby making it possible to improve the safety markedly.

<Glucose>

In addition, glucose in addition to acetic acid and acetate salt is included in the dialysis agent A of the present invention for the purpose of maintaining the glucose level of the patient. In the dialysis agent A of the present invention, degradation of glucose is suppressed by including acetic acid and acetate salt in the specific ratio as mentioned above, so that an improvement of its stability is achieved. The content of glucose in the agent A is appropriately set depending on the glucose concentration provided in the finally prepared dialysate. Specifically, the content of glucose in the dialysis agent A may be appropriately set so that the glucose concentration in the finally prepared dialysate is 0.1 to 2.5 g/L, preferably 1.0 to 2.0 g/L. More specifically, in the dialysis agent A of the present invention, glucose may be set so as to satisfy the ratio of 0.0001 to 0.0069 mole, preferably 0.0009 to 0.0055 mole, per 1 mole of total moles of acetic acid and sodium acetate.

<Other Formulation Components>

The dialysis agent A of the present invention may include physiologically available electrolytes used for dialysate, in addition to acetic acid, acetate salt, and glucose. Examples of such electrolytes include, for example, those that may be sources for magnesium ions, calcium ions, sodium ions, potassium ions, chloride ions, citrate ions, lactate ions, gluconate ions, succinate ions, malate ions, etc. It is desirable to include sources for at least sodium ions, chloride ions, magnesium ions, and calcium ions as the electrolytes (other than acetic acid and acetate salt) contained in the dialysis agent A of the present invention, and it is more desirable to further include a source for potassium ions in addition to such sources mentioned above.

As a source for magnesium ions, it includes magnesium salts. For the magnesium salt used in the dialysis agent A of the present invention, it includes, for example, but not particularly limited to, magnesium chloride, magnesium lactate, magnesium citrate, magnesium gluconate, magnesium succinate, magnesium malate, etc., as long as it is acceptable as a component of the dialysate. Among these magnesium salts, magnesium chloride is preferably used as a source for magnesium because its water solubility is high. These magnesium salts may be in the form of hydrates. Further, such magnesium salts may be used alone or in combination of two or more kinds thereof.

As a source for calcium ions, it includes calcium salts. For the calcium salt used in the dialysis agent A of the present invention, it includes, for example, but not particularly limited to, calcium chloride, calcium lactate, calcium citrate, calcium gluconate, calcium succinate, calcium malate, etc., as long as it is acceptable as a component of the dialysate. Among these calcium salts, calcium chloride is preferably used as a source for calcium because its water solubility is high. These calcium salts may be in the form of hydrates. Further, such calcium salts may be used alone or in combination of two or more kinds thereof.

As a source for sodium ions, it includes sodium salts. When sodium acetate is used as an acetate salt, the sodium acetate becomes a source for sodium ions, but sodium ions are supplemented by using also sodium salts other than sodium acetate so that a desired sodium ion concentration can be provided in the dialysate. The sodium salt includes, for example, but not particularly limited to, sodium chloride, sodium lactate, sodium citrate, sodium gluconate, sodium succinate, sodium malate, etc., as long as it is acceptable as a component of the dialysate. Among these sodium salts, sodium chloride is preferably used as a source for sodium because it is the most physiological substance. These sodium salts may be in the form of hydrates. Further, such sodium salts may be used alone or in combination of two or more kinds thereof.

As a source for potassium ions, it includes potassium salts. For the potassium salt formulated in the dialysis agent A of the present invention, it includes, for example, but not particularly limited to, potassium chloride, potassium lactate, potassium citrate, potassium gluconate, potassium succinate, potassium malate, etc., as long as it is acceptable as a component of the dialysate. Among these potassium salts, potassium chloride is preferably used as a source for potassium because it is the most physiological substance. These potassium salts may be in the form of hydrates. Further, such potassium salts may be used alone or in combination of two or more kinds thereof.

As a source for chloride ions, it includes chloride salts. For the chloride salt formulated in the dialysis agent A of the present invention, it includes, for example, but not particularly limited to, sodium chloride, calcium chloride, magnesium chloride, potassium chloride, etc., as long as it is acceptable as a component of the dialysate. These chloride salts are preferably used because their water-solubility is high and they can achieve the role as the source for sodium, potassium, magnesium or potassium. These chloride salts may be in the form of hydrates. Further, such chloride salts may be used alone or in combination of two or more kinds thereof. In addition, hydrochloric acid that also serves as a pH adjusting agent can also be used as a source for chloride ions.

The kind and the combination of the electrolytes to be formulated in the dialysis agent A of the present invention are appropriately set according to the composition of each ion to be contained in the finally prepared dialysate, but preferred examples of the electrolyte contained in the agent A (other than acetic acid and acetate salt) include the combination of sodium chloride, magnesium chloride, calcium chloride, and potassium chloride. Further, when a combination of sodium chloride, magnesium chloride, calcium chloride, and potassium chloride is used as an electrolyte, it may further contain an organic acid salt (other than acetate salt). Examples of such organic acid salt include, for example, sodium lactate, sodium gluconate, sodium citrate, sodium malate, sodium succinate, and the like. These organic acid salts may be used alone or in combination of two or more kinds thereof.

The content of each electrolyte contained in the agent A is appropriately set depending on each ion concentration provided in the finally prepared dialysate. Specifically, in view of the kind and content of acetate salts and the amount of sodium bicarbonate formulated as the agent B, the content of the electrolyte components (other than acetic acid and acetate salt) may be appropriately set in such a manner that the finally prepared dialysate will satisfy each ion concentration as shown in Table 2 below.

TABLE 2

| | Concentration in dialysate |
|---|---|
| In the case of sodium ions | 120 to 150 mEq/L, preferably 135 to 145 mEq/L |
| In the case of potassium ions | 0.5 to 3 mEq/L, preferably 1.5 to 2.5 mEq/L |

TABLE 2-continued

| | Concentration in dialysate |
|---|---|
| In the case of calcium ions | 1.5 to 4.5 mEq/L, preferably 2.5 to 3.5 mEq/L |
| In the case of magnesium ions | 0 to 2.0 mEq/L, preferably 0.5 to 1.5 mEq/L |
| In the case of citrate ions | 0 to 18 mEq/L, preferably 0 to 3 mEq/L |
| In the case of chloride ions | 90 to 135 mEq/L, preferably 100 to 120 mEq/L |
| In the case of lactate ions | 0 to 10 mEq/L |
| In the case of malate ions | 0 to 10 mEq/L |
| In the case of gluconate ions | 0 to 10 mEq/L |
| In the case of succinate ions | 0 to 10 mEq/L |
| In the case of bicarbonate ions | 20 to 40 mEq/L, preferably 25 to 35 mEq/L |

In addition, each ion concentration shown in the above Table 2 includes each ion derived from acetate salts, and the amount of the electrolyte contained in the dialysis agent A of the present invention is also determined by taking into consideration the amount of ions supplied from the acetate salts. Further, the amount of the electrolyte (other than sodium acetate) serving as a source for sodium contained in the dialysis agent A of the present invention is determined so as to satisfy the sodium ion concentration shown in the Table 2 described above, after taking into consideration the amount of sodium supplied from sodium hydrogen carbonate in the dialysis agent B and the amount of sodium supplied from sodium acetate when using sodium acetate as the acetate salt.

For example, in the dialysis agent A of the present invention, when sodium chloride, potassium chloride, magnesium chloride, and calcium chloride are used as the electrolyte other than acetic acid and acetate salts, for example, the ratio of sodium chloride may be set to 13 to 65 moles, preferably to 16 to 63 moles; potassium chloride to 0.08 to 1.5 moles, preferably to 0.25 to 1.25 moles; magnesium chloride to 0 to 0.5 moles, preferably 0.04 to 0.38 moles; and calcium chloride to 0.13 to 1.13 moles, preferably 0.21 to 0.88 moles, per 1 mole of total moles of acetic acid and sodium acetate, so that each ion concentration contained in the dialysate satisfies the range shown in the above Table 1.

The dialysis agent A of the present invention is prepared so as to have a reasonable pH range by containing acetic acid and acetate salt at a predetermined ratio, but it may separately contain a pH adjusting agent, if necessary. As the pH adjusting agent that can be used in the dialysis agent A of the present invention, it includes, for example, but not particularly limited to, liquid acids (e.g. hydrochloric acid, lactic acid, gluconic acid, etc.), solid acids (e.g. citric acid, succinic acid, fumaric acid, malic acid, glucono delta-lactone, etc.), and their sodium, potassium, calcium, magnesium salts and the like, as long as it is acceptable as a component of the dialysate.

Among these pH adjusting agents, an organic acid is preferably used. The pH adjusting agent may be used alone or in combination of two or more kinds thereof. Further, when such a pH adjusting agents is allowed to be included in the dialysis agent A of the present invention, the content thereof may be appropriately set so that the pH adjusting agent is able to satisfy the pH of the liquid A that will be described later and is obtained by dissolving the solid agent A in water, or of the liquid agent A, and the pH of the dialysate that is finally obtained.

<Dosage Form>

The dosage form of the dialysis agent A of the present invention is not particularly limited, and may be either solid or liquid form. As used herein, the solid dialysis agent A may also be referred to as "solid agent A", and the liquid dialysis agent A may also be referred to as "liquid agent A". The solid agent A is preferred as the dosage form of the dialysis agent A of the present invention, from the viewpoint of space saving, and alleviation of a burden of the operator.

The shape of the solid agent A is not particularly limited, but includes, for example, powders, granules, and the like. As for each component content in the solid agent A, it can be appropriately set so as to satisfy each ion concentration in the dialysate described above.

In addition, as for each component content in the liquid agent A, it is not particularly limited, but may be concentrated to, for example, 25 to 40 times (preferably 30 to 40 times) the concentration of each component in the finally prepared dialysate.

<pH>

The dialysis agent A of the present invention does not cause corrosion of the dialysate delivery system and the dialysis machine and ensure the safety in case of contact with the skin of workers in the clinical or manufacturing settings or in patients with dialysis at home, because acetic acid and acetate salt satisfy the above-mentioned ratio so that the pH of the liquid A obtained by dissolving the solid agent A in water or the pH of the liquid agent A becomes about 4.

As for the pH of the liquid A obtained by dissolving the solid agent A in water or of the liquid agent A, more concretely, when the dialysis agent A is concentrated to 35 times the concentration of each component in the finally prepared dialysate, to an aqueous solution state (hereinafter referred to as "35-fold concentrated agent A solution"), there is exemplified a solution having usually a pH of 3.9 to 4.6, preferably 4.1 to 4.4, and more preferably about 4.3. Here, the pH of the 35-fold concentrated agent A solution is a value measured at 25° C.

By satisfying the above-mentioned pH range with the dialysis agent A of the present invention, it is possible to ensure the stability of glucose when it is contained. It is said that glucose is generally most stable around pH 3 (The Interaction between Food Ingredients (Japanese), publisher: Shoichi NOMA, pages 5-15, editor: Mitsuo NAMIKI, Setsuro MATSUSHITA, issued May 11, 1980), and it has been confirmed that glucose is very stable in the pH range described above.

Further, by satisfying the above-mentioned pH range with the dialysis agent A of the present invention, it is also possible to effectively reduce the acetic acid odor. If the amount of the acetate salt in the dialysis agent A is less than 0.5 mole per 1 mole of acetic acid and the pH is lower than the above-mentioned pH range, the acetic acid odor tends to increase.

<Preferred Embodiment>

From the viewpoint of exerting more improved actions, such as storage stability, reduction in acetic acid odor, and suppression of corrosion of the dialysate delivery system and the dialysis machine, the dialysis agent A of the present invention is preferably one wherein the molar ratio of acetic acid and acetate salt is 1:0.5 to 2, the total amount of acetic acid and acetate salt is set to between 2 mEq or more and less than 6 mEq in the dialysis agent A required to prepare 1 L of the bicarbonate dialysate, and the pH of the 35-fold concentrated agent A solution is 3.9 to 4.6; more preferably one wherein the molar ratio of acetic acid and acetate salt is 1:0.75 to 1.5 (more preferably 1:1 to 1.5), the total amount of acetic acid and acetate salt is set to between 2 mEq or more and 5.5 mEq or less in the dialysis agent A required to prepare 1 L of the bicarbonate dialysate, and the pH of the 35-fold concentrated agent A solution is 4.1 to 4.4; and especially preferably one wherein the molar ratio of acetic acid and acetate salt is 1:1 to 1.25, the total amount of acetic acid and acetate salt is set to between 3 mEq or more and 5 mEq or less in the dialysis agent A required to prepare 1 L of the bicarbonate dialysate, and the pH of the 35-fold concentrated agent A solution is about 4.3.

<Moisture Content>

If the dialysis agent A of the present invention is a solid agent A, its moisture content is preferably 1.0% by weight or less, more preferably 0.8% by weight or less. In the dialysis agent A of the present invention, it is possible to reduce the acetic acid odor more effectively and further improve the storage stability of glucose more effectively by reducing the moisture content to the range described above.

<Production Method and Packaging>

The production method of the dialysis agent A of the present invention is not particularly limited, but is appropriately set according to the dosage form, and a suitable production method will be described below, separately for the solid agent A and the liquid agent A.

<Production Method of Solid Agent A and Packaging>

As a suitable production method of the solid agent A, it include a production method comprising a first step of mixing acetic acid and an acetate salt and a second step of mixing the mixture obtained in the first step, with glucose and other formulation components.

By preparing in advance a mixture of acetic acid and acetate salt (hereinafter, referred to as a first source in some cases) in the first step, it becomes possible to significantly reduce the acetic acid odor of the solid agent A finally obtained. Especially, in the case of using anhydrous sodium acetate, a more effective suppression of the acetic acid odor becomes possible, and thus it is preferred to use glacial acetic acid as acetic acid and anhydrous sodium acetate as the acetate salt in the production of the solid agent A.

Further, the total amount of the acetate salt contained in the solid agent A may be supplied to the preparation of the mixture in the first step, or a portion of the acetate salts contained in the solid agent A may be supplied to the preparation of the mixture in the first step and the remainder of the acetate salt may be mixed in the second step. Of the acetate salts contained in the solid agent A, the amount of the acetate salt to be supplied to the first step is not particularly limited, but, for example, it is usually 20 to 100 parts by weight, preferably 50 to 100 parts by weight, per 100 parts by weight of the total amount of acetate salts contained in the solid agent A.

Furthermore, the total amount of the acetic acid contained in the solid agent A may be supplied to the preparation of the mixture in the first step, or a portion of the acetic acid contained in the solid agent A may be supplied to the preparation of the mixture in the first step and the remainder of the acetic acid may be mixed in the second step. The acetic acid odor can be more effectively reduced as the amount of acetic acid contained in the solid agent A is increasingly supplied to the first step, and it is preferable to supply the total amount of acetic acid contained in the solid agent A to the first step. Of the acetic acid contained in the solid agent A, specifically, the amount of acetic acid to be supplied to the first step is usually 50 to 100 parts by weight, preferably 75 to 100 parts, and more preferably 100 parts by weight, per 100 parts by weight of the total amount of acetic acid contained in the solid agent A.

The method of mixing acetic acid and acetate salt in the first step is not particularly limited, but a mixing method performed under low moisture conditions, such as mixing under heating, drying, blowing, decompression processing, etc., is preferred from the viewpoint of reducing the acetic acid odor more effectively.

Since the mixture obtained in the first step emits the acetic acid odor only slightly in a low humidity environment of small moisture content, but tends to emit a strong acetic acid odor when the moisture content is large or in high humidity environments, it is possible to suppress the acetic acid odor by lowering the moisture content of the mixture in the manufacturing process or the humidity during storage. For example, it is possible to remove the moisture content by heating sodium acetate to 50 to 150° C. so that the moisture content is sufficiently reduced or by adding a moisture adsorbent such as molecular sieves to glacial acetic acid. It becomes possible to obtain a mixture with low acetic acid odor by mixing these under conditions of 60% RH or less, preferably 50% RH or less, and more preferably 40% RH or less (at 25° C. for all cases). Further, the effect of suppressing the acetic acid odor can be further improved by using a means for removing such excess moisture, such as heating to 30 to 90° C. when mixed, blowing a dry air with low absolute humidity of, for example, 1.5 g/m$^3$ or less, or decompressing, or by temporal storage in a sealed container after mixing or optional warming after mixing.

The moisture content of the mixture obtained in the first step is, for example, 1.0% by weight or less, preferably 0.8% by weight or less.

In the second step, the solid agent A is prepared by mixing the first material obtained in the first step with glucose and other formulation components. In the second step, the mixing of the mixture obtained in the first step with other formulation components may also be a simple mixing, or may be performed using wet granulation and dry granulation, such as agitating granulation, fluidized bed granulation, tumbling fluidized bed granulation, and pressure granulation.

In the second step, each of other formulation components to be mixed may be mixed individually with the first material, or a composition comprising some or all of the other components to be mixed is previously prepared and then the composition may be mixed with the first material. Preferably, there is exemplified a method wherein a composition containing an electrolyte (other than acetic acid and acetate salt) and an acetate salt as needed (hereinafter also referred to as the second material) is previously prepared and then mixed with the first material. In the case of allowing an organic acid salt to be contained in the dialysis agent A of the present invention, the organic acid salt is preferably contained in the second material. Further, the glucose may be contained in the second material, or may be mixed as a third material with the first material and the second material, with being separated from the first material and the second material. In addition, some of glucose may be mixed with the second material and the remainder may be mixed as a third material. Furthermore, in the case of mixing a portion of the acetic acid in the second step, the acetic acid may be mixed with the second material, but may be mixed as a fourth material, with being separated from the first material, the second material and optionally the third material. In addition, the organic acid other than acetic acid may be contained in at least one of the second material, the third material, and the fourth material, or may be mixed as a fifth material, with being separated from these materials.

Further, the composition subjected to the second step as the second material can be in the state of a mixture containing glucose and an electrolyte other than acetic acid and acetate salt, but can be preferably in the state of granules. The method for producing a second material in the state of granules is not particularly limited, but such a method includes, for example, the following method: when producing granules (second material) containing sodium chloride, potassium chloride, calcium chloride, and magnesium chloride as the electrolyte, an aqueous solution of calcium chloride and magnesium chloride is added to a mixture of sodium chloride and potassium chloride; the mixture is mixed under heating at 50 to 90° C.; glucose and optional other formulation components (organic acid salts etc.) are added thereto; and further mixing is performed under heating to form granules. Further, in the formation of the granules, calcium chloride and magnesium chloride in the form of powder may be added instead of adding an aqueous solution of calcium chloride and magnesium chloride, and a suitable amount of water may be added before or after the addition of such powdery calcium chloride and magnesium chloride. However, the granules should be preferably dried thoroughly even after any granulation operation is employed.

As a preferred embodiment of the second step, there is exemplified a method wherein a first material (a mixture of acetic acid and acetate salt), a second material (a composition containing an electrolyte other than acetic acid and acetate salt), a third material (glucose), an optional fourth material (acetic acid), and an optional fifth material (an organic acid other than acetic acid) are mixed under a low humidity condition (60% RH or less, preferably 50% RH or less, and more preferably 40% RH or less (at 25° C. in all cases)). At the time of mixing in the second step, similarly to the first step, a suppression effect on the reduction of the acetic acid odor can be more enhanced by using the means for removing the excess moisture, such as heating to 30 to 90° C., blowing of a dry air having a low absolute humidity, or decompression. From the viewpoint of reducing the acetic acid odor more of the solid agent A to be manufactured, it is preferred that the first material, the second material, and the third material that is added as needed are in the state of low moisture content. As a method of reducing the moisture content in this way, for example, there is exemplified a method comprising drying in advance each raw material to be supplied to the second step, at 90 to 140° C. and cooling the dried material by a cold air having an absolute humidity of 1.5 g/m$^3$ or less.

The solid agent A thus produced is optionally subjected to a drying treatment so as to have the moisture content as described above and is then provided as being accommodated in a packaging container. The packaging container used for packaging the solid agent A includes, for example, a flexible bag and a hard bottle. As the packaging container, it specifically includes silica vapor deposition laminated bag, aluminum vapor deposition laminated bag and aluminum oxide vapor deposition laminated bag, aluminum laminate bag, polyethylene hard bottle, and the like. Especially, a packaging bag using a metal foil such as an aluminum foil (aluminum laminated bag, etc.) can keep water vapor transmission at a low level and suppress more effectively acetic acid from being volatilized. In addition, the water vapor transmission of these packaging containers includes preferably 0.5 g/m$^2$·24 h (40° C., 90% RH) or less, and more preferably 0.2 g/m$^2$·24 h (40° C., 90% RH) or less from the viewpoint of reducing the acetic acid odor more effectively. The water vapor transmission is a value measured according to the measurement method specified in HS Z0208 "Testing Methods for Determination of the Water Vapor Transmission (Rate of Moisture—Proof Packaging Materials (Dish Method))".

Furthermore, in order to more effectively reduce moisture content of the solid agent A to be accommodated in the packaging container, a desiccant may be accommodated in the packaging container together with the solid agent A. The desiccant is not particularly limited, but includes, for example, zeolite, magnesium sulfate, sodium sulfate, silica gel, alumina, and the like. When the desiccant is accommodated in a packaging container, the desiccant may be combined into a part of the plastic (for example, polyethylene layers) constituting the container and such a container may be used, or a space (a separate room) to accommodate the desiccant in the packaging container may be provided. Further, the desiccant being in a state where it is placed in a nonwoven fabric so as not to mix with the solid agent A may be accommodated in a packaging container.

Production of Liquid Agent a and Packaging

The liquid agent A is prepared by weighing out a predetermined amount of acetic acid, an acetate salt, glucose, and other electrolytes, and dissolving them in water while mixing. In addition, the liquid agent A can also be prepared by dissolving in water a predetermined amount of the solid agent A described above. Further, after dissolving each formulation component in water, they may be subjected, if necessary, to a treatment such as filtration and the like.

The liquid agent A thus prepared is accommodated in a packaging container and then provided. The packaging container used for packaging the liquid agent A includes, for example, polyethylene plastic containers, such as polyethylene bottles and the like.

2. Dialysis Agent

The present invention further provides a two pack type dialysis agent comprising the dialysis agent A described above and a dialysis agent B containing sodium hydrogen carbonate.

No inclusion of electrolyte components other than sodium bicarbonate in the dialysis agent B used in the dialysis agent of the present invention is desirable and such components consisting substantially of only sodium bicarbonate are preferred.

Further, the dialysis agent B may be either solid or liquid form, but its solid form is preferable from the viewpoint of ease of transportation and storage.

If the dialysis agent B is a liquid, the content of sodium bicarbonate in the liquid dialysis agent B may be an amount capable of satisfying the desired bicarbonate ion concentration in the finally prepared dialysate, but includes, for example, 4 to 8 g/100 mL, preferably 6 to 8 g/100 mL.

In the dialysis agent of the present invention, the amount used of the dialysis agent B is preferably set so as to have a bicarbonate ion concentration of 25 to 35 mEq/L in the finally prepared dialysate, in consideration of the ratio of acetic acid and sodium acetate in the dialysis agent A, the amount of total acetate ions, and the pH of the dialysate. In particular, from the viewpoint of correction of acidosis of dialysis patients and control the total alkali amount of the dialysate to the appropriate range, a more preferable amount used of the dialysis agent B is an amount such that the bicarbonate ion concentration in the finally prepared dialysate becomes 27 to 33 mEq/L.

The dialysis agent of the present invention is used to prepare a bicarbonate dialysate. Specifically, the bicarbonate dialysate is prepared by mixing a dialysis agent A with a dialysis agent B and diluting the mixture with a predetermined amount of water (preferably purified water). If the dialysis agent A is a solid agent A, the solid agent A is dissolved as needed in an appropriate amount of water to prepare a liquid A (a concentrate), which may be used in the preparation of a dialysate. In addition, even if the dialysis agent B is a solid, the solid agent B is dissolved as needed in an appropriate amount of water to prepare a liquid B (a concentrate), which may be mixed with the dialysis agent A and a predetermined amount of water.

Further, the pH of the dialysate prepared by the dialysis agent of the present invention is not particularly limited as long as it satisfies the range that is acceptable as a dialysate, but it is preferably 7.2 to 7.6, and more preferably 7.2 to 7.5 or 7.2 to 7.4, in view of avoiding the risk of excessive correction of acidosis of dialysis patients. A pH range of such a dialysate is adjusted by appropriately setting the composition of the dialysis agent A and the use ratio of the dialysis agent A and the dialysis agent B.

EXAMPLES

Hereinafter, the present invention is specifically described by way of Examples. However, the present invention is not to be construed as being limited to the following Examples.

Test Example 1

Potassium chloride 2.61 g, calcium chloride hydrate 3.86 g, magnesium chloride hydrate 1.78 g, glucose 26.25 g, sodium chloride (a predetermined amount shown in Table 3), glacial acetic acid (a predetermined amount shown in Table 3), and anhydrous sodium acetate (a predetermined amount shown in Table 3) were dissolved in water to prepare a total volume of 500 mL of a liquid dialysis agent A. The liquid dialysis agent A is one in a state of an aqueous solution (sodium ion concentration of 3780 mEq/L) that was concentrated to 35 times the concentration of each component in the finally prepared dialysate.

TABLE 3

|  | Sodium chloride (g) | Acetic acid (g) | Sodium acetate (g) | Molar ratio of acetic acid and sodium acetate |
|---|---|---|---|---|
| Comparative Example 1 | 110.45 | 2.10 | 0 | 1:0 |
| Example 1 | 109.43 | 2.10 | 1.44 | 1:0.5 |
| Example 2 | 108.92 | 2.10 | 2.15 | 1:0.75 |
| Example 3 | 108.41 | 2.10 | 2.87 | 1:1 |
| Example 4 | 107.90 | 2.10 | 3.59 | 1:1.25 |
| Example 5 | 107.38 | 2.10 | 4.31 | 1:1.5 |
| Example 6 | 106.87 | 2.10 | 5.02 | 1:1.75 |
| Example 7 | 106.36 | 2.10 | 5.74 | 1:2 |
| Comparative Example 2 | 104.32 | 2.10 | 8.61 | 1:3 |

The pH of this liquid dialysis agent A, the amount of 5-hydroxymethyl furfural (hereinafter referred to as 5-HMF) that is a degradation product of glucose, and the concentration of volatilized acetic acid were measured. Further, each dialysis agent A was accommodated in a polyethylene bottle under accelerated test conditions (40° C./75% RH), and the amount of 5-HMF was measured after 1 to 2 months storage. The pH was measured at a liquid temperature of 25° C. by using a pH meter (manufacturer: Horiba, Ltd.; model number: F-73). As for the concentration of volatilized acetic acid, each liquid dialysis agent A was accommodated in an Erlenmeyer flask, allowed to stand for 15 minutes to set a gas detector tube for the acetic acid measurement over the liquid surface, and a fixed amount of a gaseous sample was passed through the gas detector tube so that the concentration of volatilized acetic acid was measured by a gas detector tube type gas measuring instrument (manufacturer: GASTEC, model number: GV-100S). In addition, with respect to the amount of 5-HMF, the absorbance of 5-HMF at the absorption wavelength (wavelength 284 nm) on the filtrate that was obtained by filtration with a 0.2 μm filter was measured using a spectrophotometer.

In addition, a bicarbonate dialysate was prepared by weighing a liquid dialysis agent A 10 mL accurately, adding purified water thereto to a volume of about 300 ml, adding a dialysis agent B (sodium hydrogen carbonate) 0.94 g to the mixture (the bicarbonate ion concentration in the dialysate was 32 mEq/L), and adding purified water thereto to accurately make a volume of 350 ml. All of the obtained bicarbonate dialysates (the liquid dialysis agents A in Examples 1 to 7 and Comparative Examples 1 to 2 were used.) contain sodium ions of 140 mEq/L, potassium ions of 2 mEq/L, calcium ions of 3 mEq/L, magnesium ions of 1 mEq/L. The pH and the ionized calcium concentration of the bicarbonate dialysate obtained were measured. The pH was measured by using a pH meter (manufacturer: Horiba, Ltd.; model number: F-73) at a liquid temperature of 25° C. and the ionized calcium concentration was measured by using a blood gas analyzer cobas b121 (manufacturer: Roche Diagnostics).

The results of measuring the pH, the amount of 5-HMF, and the concentration of volatilized acetic acid on the liquid dialysis agent A after the preparation are shown in Table 4, and the results of measuring the amount of 5-HMF after the accelerated test are shown in Table 5. Furthermore, for the resulting bicarbonate dialysate, the measurement results of the concentration of total acetate ions contained, the pH, and the ionized calcium concentration are shown in Table 6.

As is apparent from Table 4, in the liquid dialysis agent A (Comparative Example 1) having a molar ratio of 1:0 of acetic acid:acetate salt, the pH was as low as 2.31 that was strongly acidic, because of which it was not possible to secure sufficient safety in the handling. Further, the volatilized acetic acid concentration itself of the liquid dialysis agent A was not high, but clearly higher than in other Comparative Example 2 and Examples, resulting in observation of a strong unpleasant smell. In other words, the liquid dialysis agent A of Comparative Example 1 was a formulation, such that there was a concern about corrosion of the dialysate delivery system and the dialysis machine. Furthermore, the absorbance of the liquid dialysis agent A of Comparative Example 1 at 284 nm of the absorption wavelength of 5-HMF was already higher even after the preparation than other Examples and was remarkably higher after the accelerated test. This indicates that the liquid dialysis agent A with a low pH has not been able to maintain glucose stably.

Further, the ionized calcium concentration of the liquid dialysis agent A (Comparative Example 2) having a 1:more than 2 molar ratio of acetic acid:acetate salt was decreased compared with Comparative Example 1 and the other Examples.

Each liquid dialysis agent A (Examples 1 to 7) having a molar ratio within a range of 1:0.5 to 2 had a pH of 3.9 or more, could be handled safely in clinical settings, and was free from the worry about the corrosion of the dialysate delivery system and the analyzer. In addition, the absorbance of the liquid dialysis agents A of each of Examples 1 to 7 at 284 nm of the wavelength for 5-HMF showed a lower value after the preparation and after the accelerated test, than that of Comparative Example 1, indicating that glucose degradation could be sufficiently suppressed.

Furthermore, the bicarbonate dialysate prepared by using the liquid dialysis agent A of each of Examples 1 to 7 has a total acetate ion concentration of between 2 mEq/L or more and less than 6 mEq/L and maintains a suitable pH as a dialysate, and moreover was able to maintain the ionized calcium concentration at a high level in comparison with Comparative Example 2.

TABLE 4

| | pH of liquid dialysis agent A | Absorbance of liquid dialysis agent A (284 nm) | Volatilized acetic acid concentration (ppm) |
|---|---|---|---|
| Comparative Example 1 | 2.31 | 0.0039 | 36 |
| Example 1 | 3.94 | 0.0028 | 28 |
| Example 2 | 4.12 | 0.0028 | 28 |
| Example 3 | 4.25 | 0.0028 | 30 |
| Example 4 | 4.35 | 0.0027 | Not measured |
| Example 5 | 4.43 | 0.0025 | 25 |
| Example 6 | 4.51 | 0.0023 | Not measured |
| Example 7 | 4.56 | 0.0021 | 28 |
| Comparative Example 2 | 4.78 | 0.0019 | 30 |

TABLE 5

| | Absorbance (284 nm) | |
|---|---|---|
| | After one month | After two months |
| Comparative Example 1 | 0.0237 | 0.0519 |
| Example 1 | 0.0195 | 0.0332 |
| Example 2 | 0.0174 | 0.0298 |
| Example 3 | 0.0161 | 0.0275 |
| Example 5 | 0.0159 | 0.0257 |
| Example 7 | 0.0131 | 0.0232 |
| Comparative Example 2 | 0.0116 | 0.0212 |

TABLE 6

| | Bicarbonate dialysate | | |
|---|---|---|---|
| Liquid dialysis agent A used | Total acetate ion concentration (mEq/L) | pH | Ionized calcium concentration (mmol/L) |
| Comparative Example 1 | 2 | 7.39 | 1.485 |
| Example 1 | 3 | 7.39 | 1.476 |
| Example 2 | 3.5 | 7.40 | 1.475 |
| Example 3 | 4 | 7.39 | 1.462 |
| Example 4 | 4.5 | 7.39 | 1.442 |
| Example 5 | 5 | 7.40 | 1.439 |
| Example 6 | 5.5 | 7.39 | 1.429 |
| Example 7 | 5.997 | 7.39 | 1.429 |
| Comparative Example 2 | 8 | 7.39 | 1.397 |

Test Example 2

(1) Preparation of Liquid Dialysis Agent A

The liquid dialysis agent A of each of Comparative Examples 3 to 5 was prepared by the following method. In addition, the liquid dialysis agent A of each of Examples 1 to 7 and Comparative Examples 1 to 2 shown in Test Example 1 was prepared again.

Comparative Example 3

Potassium chloride 2.61 g, calcium chloride hydrate 3.86 g, magnesium chloride hydrate 1.78 g, glucose 26.25 g, sodium chloride 106.97 g, anhydrous citric acid 1.79 g, and sodium citrate hydrate 0.69 g were dissolved in water to prepare a total volume of 500 mL of a liquid dialysis agent A. The liquid dialysis agent A is one in a state of an aqueous solution (sodium ion concentration of 3675 mEq/L) that was concentrated to 35 times the concentration of each component in the finally prepared dialysate.

Comparative Example 4

Potassium chloride 2.61 g, calcium chloride hydrate 3.22 g, magnesium chloride hydrate 1.78 g, glucose 17.50 g, sodium chloride 106.87 g, glacial acetic acid 2.63 g, and anhydrous sodium acetate 7.89 g were dissolved in water to prepare a total volume of 500 mL of a liquid dialysis agent A. The liquid dialysis agent A is one in a state of an aqueous solution (sodium ion concentration of 3850 mEq/L) that was concentrated to 35 times the concentration of each component in the finally prepared dialysate.

Comparative Example 5

Potassium chloride 2.61 g, calcium chloride hydrate 3.22 g, magnesium chloride hydrate 1.78 g, glucose 26.25 g, sodium chloride 106.87 g, glacial acetic acid 2.63 g, and anhydrous sodium acetate 7.89 g were dissolved in water to prepare a total volume of 500 mL of a liquid dialysis agent A. The liquid dialysis agent A is one in a state of an aqueous solution (sodium ion concentration of 3850 mEq/L) that was concentrated to 35 times the concentration of each component in the finally prepared dialysate.

(2) Evaluation of pH and 5-HMF Amount of Liquid Dialysis Agent A

With respect to each liquid dialysis agent A obtained above, the pH after the preparation and the amount of 5-HMF that is a degradation product of glucose, as well as the amount of 5-HMF after one to two months storage under the accelerated test conditions (40° C./75% RH) were measured in the same manner as in Test Example 1.

The results that were obtained are shown in Table 7. As is apparent from Table 7, the liquid dialysis agent A (Comparative Example 1) having a 1:0 molar ratio of acetic acid:sodium acetate, and the liquid dialysis agent A (Comparative Example 3) wherein citric acid and sodium citrate were combined in place of acetic acid and sodium acetate showed a strong acidity of less than pH 3, because of which it was not able to secure sufficient safety in handling. On the other hand, each liquid dialysis agent A (Examples 1 to 7) having a molar ratio within a range of 1:0.5 to 2 of acetic acid:sodium acetate had a pH of 3.9 or more, could be handled safely in clinical settings, and were free from the worry about the corrosion of the dialysate delivery system and the analyzer. In addition, the absorbance of the liquid dialysis agent A of each of Examples 1 to 7 at 284 nm of the wavelength for 5-HMF showed a lower value immediately after the preparation and after the accelerated test, than that of each of Comparative Examples 1 and 3, indicating that glucose degradation could be sufficiently suppressed.

TABLE 7

| | Molar ratio of acetic acid and sodium acetate | pH of liquid dialysis agent A | Absorbance of liquid dialysis agent A (284 nm) | | |
|---|---|---|---|---|---|
| | | | Start time | After one month | After two months |
| Comparative Example 1 | 1:0 | 2.31 | 0.0050 | 0.0327 | 0.0631 |
| Example 1 | 1:0.5 | 3.94 | 0.0034 | 0.0252 | 0.0476 |
| Example 2 | 1:0.75 | 4.12 | 0.0033 | 0.0230 | 0.0435 |
| Example 3 | 1:1 | 4.25 | 0.0031 | 0.0213 | 0.0408 |
| Example 4 | 1:1.25 | 4.35 | 0.0029 | 0.0195 | 0.0344 |
| Example 5 | 1:1.5 | 4.43 | 0.0028 | 0.0185 | 0.0324 |
| Example 6 | 1:1.75 | 4.50 | 0.0028 | 0.0183 | 0.0314 |
| Example 7 | 1:2 | 4.57 | 0.0027 | 0.0175 | 0.0296 |
| Comparative Example 2 | 1:3 | 4.76 | 0.0026 | 0.0155 | 0.0257 |
| Comparative Example 3 | 0:0 (having a 4:1 molar ratio of citric acid and sodium citrate) | 2.34 | 0.0050 | 0.0429 | 0.0849 |
| Comparative Example 4 | 1:2.2 | 4.63 | 0.0023 | 0.0120 | 0.0203 |
| Comparative Example 5 | 1:2.2 | 4.62 | 0.0027 | 0.0170 | 0.0287 |

Test Example 3

For each liquid dialysis agent A of Examples 1 to 7 and Comparative Examples 1 to 2 prepared in the above Test Example 2, the volatilized acetic acid concentration was measured in the following manner.

First, a liquid dialysis agent A 700 mL was charged gently into a 1000 ml-glass container A equipped with a stirrer, and the upper part of this glass container A was sealed with a stopper in communication with a glass tube X and a glass tube $Y_1$. One end of the glass tube X is exposed in the air out of the glass container A, and the other end is in a state of being immersed in the liquid dialysis agent A in the glass container A. Further, one end of the glass tube $Y_1$ is in a state of being exposed in the gas phase of the glass container A.

Separately, 0.001M aqueous sodium hydroxide solution 300 mL and a few drops of phenolphthalein solution were charged into a 500 mL-glass container B, and the upper part of this glass container B was sealed with a stopper in communication with a glass tube $Y_2$ and a glass tube Z. One end of the glass tube $Y_2$ is connected to the glass tube $Y_1$ through a rubber tube.

And, the other end of the glass tube $Y_2$ is in a state of being immersed in the aqueous sodium hydroxide solution in the glass container B. Further, one end of the glass tube Z is exposed in the air out of the glass container B, and the other end is connected to an aspirator (manufacturer: ADVANTEC; model number: 08090137).

By using the apparatus configured as described above, the liquid dialysis agent A was suctioned by an aspirator while stirring with a stirrer for 10 minutes at a rate of 15 L/min. By absorbing the acetic acid evaporated from the liquid dialysis agent A in the glass container A, into the aqueous sodium hydroxide solution in the glass container B in this manner, the volatilized acetic acid was captured. Then, the amount of volatilized acetic acid of the liquid dialysis agent A was determined by the titration of the aqueous sodium hydroxide solution in the glass container B with 0.005M hydrochloric acid.

The results obtained are shown in Table 8. This result also revealed that, similarly to the results of the above Test Example 1, the amount of volatilized acetic acid of the liquid dialysis agent A of each of Examples 1 to 7 was small compared to that of the liquid dialysis agent A of Comparative Example 1. When use of a large amount of dialysate handled in the dialysis facilities is assumed, it can be said that there can be an evident difference of the liquid dialysis agent A of each of Examples 1 to 7 in terms of improvement of the working environment (reduction of unpleasant odor), in comparison with Comparative Example 1.

TABLE 8

| | Molar ratio of acetic acid and sodium acetate | Amount of volatilized acetic acid (mg) |
|---|---|---|
| Comparative Example 1 | 1:0 | 9.48 |
| Example 1 | 1:0.5 | 8.64 |
| Example 2 | 1:0.75 | 8.69 |
| Example 3 | 1:1 | 8.62 |
| Example 4 | 1:1.25 | 8.66 |
| Example 5 | 1:1.5 | 8.41 |
| Example 6 | 1:1.75 | 8.38 |
| Example 7 | 1:2 | 8.26 |
| Comparative Example 2 | 1:3 | 8.33 |

Test Example 4

(1) Preparation of Liquid Dialysis Agent A

The liquid dialysis agent A of Comparative Example 6 was prepared by the following method. In addition, each liquid dialysis agent A of Examples 2 to 7 and Comparative Examples 1 to 2 shown in the Test Example 1, as well as the liquid dialysis agent A of Comparative Example 3 shown in the Test Example 2 was prepared again.

Comparative Example 6

Potassium chloride 2.61 g, calcium chloride hydrate 3.86 g, magnesium chloride hydrate 1.78 g, glucose 26.25 g, sodium chloride 106.36 g, 6M hydrochloric acid 5.83 mL and anhydrous sodium acetate 5.74 g were dissolved in water to prepare a total volume of 500 mL of a liquid dialysis agent A. The liquid dialysis agent A is one in a state of an aqueous solution (sodium ion concentration of 3780 mEq/L) that was concentrated to 35 times the concentration of each component in the finally prepared dialysate.

(2) Evaluation of pH and Corrosion of Liquid Dialysis Agent A

With respect to each liquid dialysis agent A obtained above, the pH after the preparation was measured in the same manner as in Test Example 1. In addition, corrosive properties of the liquid dialysis agent A obtained above to stainless steel were evaluated by the following method. Each liquid dialysis agent A 100 mL was placed in a 200 ml-transparent styrol container, and an almost half area of 40 mm×100 mm of a stainless steel (SUS304) plate was allowed to stand to soak in the liquid dialysis agent A, after which time a lid was put on the transparent styrol container and the plate was left at room temperature for two months. One month and two months after the storage, the concentration of iron in the liquid dialysis agent A was measured. The measurement of iron concentration was performed according to the Method A that is defined in "General Tests 1. Chemical Methods 1.10 Iron Limit Tests" of The Japanese Pharmacopoeia, Sixteenth Edition. Specific measurement conditions are as follows. An acetic acid-sodium acetate buffer 5 mL for iron limit test and an L-ascorbic acid solution 2 mL (1 g→100 mL) were added to the liquid dialysis agent A 5 mL, then mixed, and allowed to stand for 30 minutes. Next, a solution 1 mL (0.25 g→50 mL) of 2,2'-bipyridylethanol in ethanol (95) was added thereto, water was added thereto to make up a volume of 50 mL accurately, and the mixture was allowed to stand for 30 minutes, thereby to obtain a sample solution. An iron reference standard solution 2 mL of the Japanese Pharmacopoeia (Japanese Pharmacopoeia 0.01 mg/mL) was used as the reference standard solution. For the sample solution and the standard solution, the absorbance at an absorption wavelength (wavelength 522 nm) was measured using a spectrophotometer to calculate the iron concentration. The evaluation of corrosive properties was performed in n=2, thereby to calculate the average value of iron concentration in the liquid dialysis agent A.

The results obtained are shown in Table 9. As is apparent from Table 9, in the liquid dialysis agents A of Comparative Examples 1 and 3 wherein the pH was low, the iron concentration was high, and corrosion of the stainless steel plate was in progress. Further, although the pH in the liquid dialysis agent A of Comparative Example 6 containing HCl was 4.26, the iron concentration was high and an apparent corrosion of the stainless steel plate was observed, because of which this was a formulation for which the corrosion of the dialysate delivery system and the dialysis machine was concerned. In contrast, in each liquid dialysis agent A of Examples 2 to 7, the iron concentration after storage was maintained at a low value, and the corrosion of the dialysate delivery system and the dialysis machine could be suppressed. In addition, even if the liquid dialysis agent A of Example 1 was used, the suppressing effect on the corrosion of the stainless steel plate was similarly observed.

TABLE 9

| | pH of liquid dialysis agent A | Iron concentration in liquid dialysis agent A (mg/L) | |
|---|---|---|---|
| | | After one month | After two months |
| Comparative Example 1 | 2.32 | 6.67 | 13.58 |

TABLE 9-continued

| | pH of liquid dialysis agent A | Iron concentration in liquid dialysis agent A (mg/L) | |
|---|---|---|---|
| | | After one month | After two months |
| Example 2 | 4.14 | 0.39 | 0.80 |
| Example 3 | 4.25 | 0.39 | 0.68 |
| Example 4 | 4.37 | 0.43 | 0.95 |
| Example 5 | 4.46 | 0.38 | 0.99 |
| Example 6 | 4.50 | 0.40 | 0.96 |
| Example 7 | 4.57 | 0.40 | 0.75 |
| Comparative Example 2 | 4.77 | 0.35 | 0.57 |
| Comparative Example 3 | 2.37 | 0.87 | 1.86 |
| Comparative Example 6 | 4.26 | 5.02 | 12.98 |

Test Example 5

(1) Preparation of Solid Dialysis Agent A

Each solid dialysis agent A of Examples 8 to 16 and Comparative Examples 7 to 8 was prepared by the following method.

Example 8

First, sodium chloride 11.15 kg, potassium chloride 0.261 kg, calcium chloride hydrate 0.386 kg, and magnesium chloride hydrate 0.178 kg were mixed under heating, followed by granulation after addition of water 0.178 kg to form granules, and the granules were dried at 130° C. to obtain an electrolyte composition. Further, separately, glacial acetic acid 0.105 kg and anhydrous sodium acetate 0.144 kg were mixed to give an acetic acid/sodium acetate mixture. The above electrolyte composition 239.4 g, the acetic acid/sodium acetate mixture 4.97 g, glacial acetic acid 2.10 g, and glucose 52.5 g were mixed with stirring to obtain a solid dialysis agent A. The molar ratio of acetic acid:sodium acetate in the solid dialysis agent A obtained is 1:0.5.

Example 9

First, sodium chloride 11.10 kg, potassium chloride 0.261 kg, calcium chloride hydrate 0.386 kg, and magnesium chloride hydrate 0.178 kg were mixed under heating, followed by granulation after addition of water 0.178 kg to form granules, and the granules were dried at 130° C. to obtain an electrolyte composition. Further, separately, glacial acetic acid 0.105 kg and anhydrous sodium acetate 0.144 kg were mixed to give an acetic acid/sodium acetate mixture. The above electrolyte composition 238.4 g, the acetic acid/sodium acetate mixture 7.46 g, glacial acetic acid 1.05 g, and glucose 52.5 g were mixed with stirring to obtain a solid dialysis agent A. The molar ratio of acetic acid:sodium acetate in the solid dialysis agent A obtained is 1:0.75.

Example 10

First, sodium chloride 11.05 kg, potassium chloride 0.261 kg, calcium chloride hydrate 0.386 kg, and magnesium chloride hydrate 0.178 kg were mixed under heating, followed by granulation after addition of water 0.178 kg to form granules, and the granules were dried at 130° C. to obtain an electrolyte composition. Further, separately, glacial acetic acid 0.105 kg and anhydrous sodium acetate 0.144 kg were mixed to give an acetic acid/sodium acetate mixture. The above electrolyte composition 237.4 g, the acetic acid/sodium acetate mixture 9.95 g, and glucose 52.5 g were mixed with stirring to obtain a solid dialysis agent A. The molar ratio of acetic acid:sodium acetate in the solid dialysis agent A obtained is 1:1.

Example 11

First, sodium chloride 10.99 kg, potassium chloride 0.261 kg, calcium chloride hydrate 0.386 kg, magnesium chloride hydrate 0.178 kg, and anhydrous sodium acetate 0.072 kg were mixed under heating, followed by granulation after addition of water 0.178 kg to form granules, and the granules were dried at 130° C. to obtain an electrolyte composition. Further, separately, glacial acetic acid 0.105 kg and anhydrous sodium acetate 0.144 kg were mixed to give an acetic acid/sodium acetate mixture. The above electrolyte composition 237.8 g, the acetic acid/sodium acetate mixture 9.95 g, and glucose 52.5 g were mixed with stirring to obtain a solid dialysis agent A. The molar ratio of acetic acid:sodium acetate in the solid dialysis agent A obtained is 1:1.25.

Example 12

First, sodium chloride 10.94 kg, potassium chloride 0.261 kg, calcium chloride hydrate 0.386 kg, magnesium chloride hydrate 0.178 kg, and anhydrous sodium acetate 0.144 kg were mixed under heating, followed by granulation after addition of water 0.178 kg to form granules, and the granules were dried at 130° C. to obtain an electrolyte composition. Further, separately, glacial acetic acid 0.105 kg and anhydrous sodium acetate 0.144 kg were mixed to give an acetic acid/sodium acetate mixture. The above electrolyte composition 238.2 g, the acetic acid/sodium acetate mixture 9.95 g, and glucose 52.5 g were mixed with stirring to obtain a solid dialysis agent A. The molar ratio of acetic acid:sodium acetate in the solid dialysis agent A obtained is 1:1.5.

Example 13

First, sodium chloride 10.89 kg, potassium chloride 0.261 kg, calcium chloride hydrate 0.386 kg, magnesium chloride hydrate 0.178 kg, and anhydrous sodium acetate 0.215 kg were mixed under heating, followed by granulation after addition of water 0.178 kg to form granules, and the granules were dried at 130° C. to obtain an electrolyte composition. Further, separately, glacial acetic acid 0.105 kg and anhydrous sodium acetate 0.144 kg were mixed to give an acetic acid/sodium acetate mixture. The above electrolyte composition 238.6 g, the acetic acid/sodium acetate mixture 9.95 g, and glucose 52.5 g were mixed with stirring to obtain a solid dialysis agent A. The molar ratio of acetic acid:sodium acetate in the solid dialysis agent A obtained is 1:1.75.

Example 14

First, sodium chloride 10.84 kg, potassium chloride 0.261 kg, calcium chloride hydrate 0.386 kg, magnesium chloride hydrate 0.178 kg, and anhydrous sodium acetate 0.287 kg were mixed under heating, followed by granulation after addition of water 0.178 kg to form granules, and the granules were dried at 130° C. to obtain an electrolyte composition. Further, separately, glacial acetic acid 0.105 kg and anhydrous sodium acetate 0.144 kg were mixed to give an acetic acid/sodium acetate mixture. The above electrolyte composition 239.1 g, the acetic acid/sodium acetate mixture 9.94 g, and glucose 52.5 g were mixed with stirring to obtain a solid dialysis agent A. The molar ratio of acetic acid:sodium acetate in the solid dialysis agent A obtained is 1:2.

Example 15

First, sodium chloride 11.66 kg, potassium chloride 0.261 kg, calcium chloride hydrate 0.386 kg, and magnesium chloride hydrate 0.178 kg were mixed under heating, followed by granulation after addition of water 0.178 kg to form granules, and the granules were dried at 130° C. to obtain an electrolyte composition. Further, separately, glacial acetic acid 0.105 kg and anhydrous sodium acetate 0.144 kg were mixed to give an acetic acid/sodium acetate mixture. The above electrolyte composition 249.7 g, the acetic acid/sodium acetate mixture 4.97 g, and glucose 52.5 g were mixed with stirring to obtain a solid dialysis agent A. The molar ratio of acetic acid:sodium acetate in the solid dialysis agent A obtained is 1:1.

Example 16

First, sodium chloride 11.58 kg, potassium chloride 0.261 kg, calcium chloride hydrate 0.386 kg, magnesium chloride hydrate 0.178 kg, and anhydrous sodium acetate 0.072 kg were mixed under heating, followed by granulation after addition of water 0.178 kg to form granules, and the granules were dried at 130° C. to obtain an electrolyte composition. Further, separately, glacial acetic acid 0.105 kg and anhydrous sodium acetate 0.144 kg were mixed to give an acetic acid/sodium acetate mixture. The above electrolyte composition 249.6 g, the acetic acid/sodium acetate mixture 6.22 g, and glucose 52.5 g were mixed with stirring to obtain a solid dialysis agent A. The molar ratio of acetic acid:sodium acetate in the solid dialysis agent A obtained is 1:1.4.

Comparative Example 7

First, sodium chloride 11.25 kg, potassium chloride 0.261 kg, calcium chloride hydrate 0.386 kg, and magnesium chloride hydrate 0.178 kg were mixed under heating, followed by granulation after addition of water 0.178 kg to form granules, and the granules were dried at 130° C. to obtain an electrolyte composition. Then, the above electrolyte composition 241.5 g, glacial acetic acid 4.20 g, and glucose 52.5 g were mixed with stirring to obtain a solid dialysis agent A. The molar ratio of acetic acid:sodium acetate in the solid dialysis agent A obtained is 1:0.

Comparative Example 8

First, sodium chloride 10.64 kg, potassium chloride 0.261 kg, calcium chloride hydrate 0.386 kg, magnesium chloride hydrate 0.178 kg, and anhydrous sodium acetate 0.574 kg were mixed under heating, followed by granulation after addition of water 0.178 kg to form granules, and the granules were dried at 130° C. to obtain an electrolyte composition. Then, the above electrolyte composition 240.7 g, glacial acetic acid 4.20 g, anhydrous sodium acetate 5.74 g, and glucose 52.5 g were mixed with stirring to obtain a solid dialysis agent A. The molar ratio of acetic acid:sodium acetate in the solid dialysis agent A obtained is 1:3.

(2) Evaluation of Solid Dialysis Agent A
(Volatilized Acetic Acid Concentration and Moisture Content of Solid Dialysis Agent A)

For each solid dialysis agent A obtained above, the volatilized acetic acid concentration was measured. Such volatilized acetic acid concentration was measured by accommodating each solid dialysis agent A in a predetermined amount shown in Table 10, into a silica deposition laminated bag, setting a gas detector tube over the agent A, passing a fixed amount of a gaseous sample through the gas detector tube, and performing the measurement by a gas detector tube type gas measuring instrument (manufacturer: GASTEC, model number: GV-100S).

Furthermore, for each solid dialysis agent A of Examples 11, 13, 15, and 16, the moisture content was measured by using a Karl Fischer moisture meter (manufacturer: Hiranuma Sangyo Corp., model number: AVQ-6).

(pH and 5-HMF amount of 35-fold concentrated agent A solution)

Further, a 35-fold concentrated agent A solution was prepared by dissolving in purified water the each solid dialysis agent A obtained above to an aqueous solution state wherein such an agent A was concentrated to 35 times the concentration of each component in the finally prepared dialysate. Specifically, the 35-fold concentrated agent A solution was prepared by dissolving in purified water a predetermined amount shown in Table 10 of each solid dialysis agent A, to a volume of 500 mL.

TABLE 10

| Solid dialysis agent A used | Amount (g) of solid dialysis agent A subjected to measurement of volatilized acetic acid concentration and moisture content and amount (g) of solid dialysis agent A dissolved in purified water. |
|---|---|
| Example 8 | 149.5 |
| Example 9 | 149.7 |
| Example 10 | 149.9 |
| Example 11 | 150.1 |
| Example 12 | 150.3 |
| Example 13 | 150.5 |
| Example 14 | 150.8 |
| Example 15 | 153.6 |
| Example 16 | 154.1 |
| Comparative Example 7 | 149.1 |
| Comparative Example 8 | 151.6 |

The pH and 5-HMF amount of the 35-fold concentrated agent A solution obtained were measured in the same manner as in Test Example 1 described above.

(pH of Bicarbonate Dialysate and Ionized Calcium Concentration)

A bicarbonate dialysate was prepared by the following method using the 35-fold concentrated agent A solution (sodium ion concentration of 3850 mEq/L) obtained from the solid dialysis agent A of each of Examples 8 to 14 and Comparative Examples 7 to 8. Each 35-fold concentrated agent A solution was accurately weighed in an amount of 10 mL; purified water was added thereto to make up a volume of about 300 mL; 0.88 g of a dialysis agent B (sodium hydrogen carbonate) was added thereto (a bicarbonate ion concentration of 30 mEq/L in the dialysate); and purified water was added thereto to accurately make up a volume of 350 mL to prepare a bicarbonate dialysis solution. The bicarbonate dialysates obtained all include sodium ions of 140 mEq/L, potassium ions of 2 mEq/L, calcium ions of 3 mEq/L, and magnesium ions of 1 mEq/L.

Further, a bicarbonate dialysate was prepared by the following method using the 35-fold concentrated agent A solution obtained from the solid dialysis agent A of each of Examples 15 and 16. Each 35-fold concentrated agent A solution was accurately weighed in an amount of 10 mL; purified water was added thereto to make up a volume of about 300 mL; 0.74 g of a dialysis agent B (sodium hydrogen carbonate) was added thereto (a bicarbonate ion concentration of 25 mEq/L in the dialysate); and purified water was added thereto to accurately make up a volume of 350 mL to prepare a bicarbonate dialysis solution. The bicarbonate dialysates obtained all include sodium ions of 140 mEq/L, potassium ions of 2 mEq/L, calcium ions of 3 mEq/L, and magnesium ions of 1 mEq/L.

The pH and the ionized calcium concentration of each bicarbonate dialysate obtained were measured in the same manner as in the above Test Example 1.

(Results)

The results of measuring the volatilized acetic acid concentration in the solid dialysis agent A and the results of measuring the pH of the 35-fold concentrated agent A solution are shown in Table 11. Further, for each of bicarbonate dialysates obtained, the measurement results of the concentration of total acetate ions contained and pH, as well as ionized calcium concentration are shown in Table 12.

As is apparent from Table 11, in the 35-fold concentrated agent A solution prepared from the solid dialysis agent A (Comparative Example 7) having a molar ratio of 1:0 of acetic acid:acetate salt, it had a low pH of about 2.5, was strongly acidic, could not ensure a sufficient safety of the handling, and was a formulation for which the corrosion of the dialysate delivery system and the dialysis machine was concerned. In addition, the absorbance of the 35-fold concentrated agent A solution prepared from the solid dialysis agent A of Comparative Example 7 at 284 nm of the absorption wavelength of 5-HMF was already higher even after the preparation than other Examples, and glucose was not able to be stably maintained. Further, in the solid dialysis agent A of Comparative Example 7, the volatilized acetic acid concentration exceeded 1000 ppm that was an unacceptable level in the clinical settings. Moreover, in spite of the molar ratio of 1:3 of acetic acid:acetate salt in the solid dialysis agent A of Comparative Example 8, the volatilized acetic acid concentration showed a high value of 700 ppm.

As can be seen from Table 12, in the bicarbonate dialysate prepared from the solid dialysis agent A (Comparative Example 8) having a molar ratio of more than 1:2 of acetic acid:acetate salt, the ionized calcium concentration was more reduced in comparison with Comparative Example 7 and other Examples.

In comparison with these Comparative Examples, the 35-fold concentrated agent A solution prepared from the solid dialysis agent A (Examples 8 to 14) having a molar ratio within a range of 1:0.5 to 2 of acetic acid:acetate salt showed a pH of 3.9 or more, could be handled safely in the clinical settings, and had no worry about the corrosion of the dialysate delivery system and the dialysis machine. Also, the 35-fold concentrated agent A solution prepared from the solid dialysis agent A (Examples 8 to 14) showed a lower value of the absorbance at a wavelength of 284 nm for 5-HMF after the preparation when compared to Comparative Example 7, and glucose degradation has been sufficiently suppressed. Further, in the solid dialysis agent A of each of Examples 8 to 14, the volatilized acetic acid concentration was lower than that of each of Comparative Examples 7 and 8. In particular, Examples 9 to 16 (acetic acid:acetate salt=1:0.75 to 2), especially Examples 10 to 16 (acetic acid:acetate salt=1:1 to 2), showed significantly lower values of the volatilized acetic acid concentration, and were remarkably excellent. Furthermore, in the bicarbonate dialysate prepared from the solid dialysis agent A of each of Examples 8 to 14, the total acetate ion concentration was between 2 mEq/L or more and less than 6 mEq/L to maintain a pH suitable as a dialysate, and the ionized calcium concentration has been able to be maintained at a high level compared with Comparative Example 8.

TABLE 11

| | Molar ratio of acetic acid:sodium acetate in solid dialysis agent A | Volatilized acetic acid concentration (ppm) of solid dialysis agent A | Moisture content (% by weight) of solid dialysis agent A | pH of 35-fold concentrated agent A solution | Absorbance (284 nm) of 35-fold concentrated agent A solution |
|---|---|---|---|---|---|
| Comparative Example 7 | 1:0 | >1000 | Not measured | 2.55 | 0.0061 |
| Example 8 | 1:0.5 | 600 | Not measured | 4.04 | 0.0057 |
| Example 9 | 1:0.75 | 300 | Not measured | 4.19 | 0.0052 |
| Example 10 | 1:1 | 30 | Not measured | 4.30 | 0.0046 |
| Example 11 | 1:1.25 | 35 | 0.65 | 4.39 | 0.0045 |
| Example 12 | 1:1.5 | 35 | Not measured | 4.48 | 0.0040 |
| Example 13 | 1:1.75 | 18 | 0.55 | 4.53 | 0.0035 |
| Example 14 | 1:2 | 20 | Not measured | 4.58 | 0.0033 |
| Example 15 | 1:1 | 20 | 0.75 | 4.30 | 0.0022 |
| Example 16 | 1:1.4 | 40 | 0.70 | 4.44 | 0.0021 |
| Comparative Example 8 | 1:3 | 700 | Not measured | 4.81 | 0.0022 |

TABLE 12

| | Bicarbonate dialysate | | |
|---|---|---|---|
| Dialysis agent used | Total acetate ion concentration (mEq/L) | pH | Ionized calcium concentration (mmol/L) |
| Comparative Example 7 | 2 | 7.42 | 1.471 |
| Example 8 | 3 | 7.39 | 1.431 |
| Example 9 | 3.5 | 7.38 | 1.414 |
| Example 10 | 4 | 7.40 | 1.378 |
| Example 11 | 4.5 | 7.39 | 1.370 |
| Example 12 | 5 | 7.40 | 1.368 |
| Example 13 | 5.5 | 7.38 | 1.349 |
| Example 14 | 5.997 | 7.39 | 1.317 |
| Example 15 | 2 | 7.58 | 1.444 |

TABLE 12-continued

| | Bicarbonate dialysate | | |
|---|---|---|---|
| Dialysis agent used | Total acetate ion concentration (mEq/L) | pH | Ionized calcium concentration (mmol/L) |
| Example 16 | 3 | 7.51 | 1.481 |
| Comparative Example 8 | 8 | 7.38 | 1.305 |

The bicarbonate concentration of the bicarbonate dialysate prepared by using each dialysis agent A of Examples 8 to 14 and Comparative Examples 7 and 8 is 30 mEq/L.
The bicarbonate concentration of the bicarbonate dialysate prepared by using each dialysis agent A of Examples 15 and 16 is 25 mEq/L.

Test Example 6

(1) Preparation of Solid Dialysis Agent A

The solid dialysis agent A of each of Examples 17 and 18 was prepared by the following method. In addition, the solid dialysis agent A of each of Examples 8 to 16 and Comparative Example 7 shown in the above Test Example 5 was prepared again.

Example 17

First, sodium chloride 10.99 kg, potassium chloride 0.261 kg, calcium chloride hydrate 0.386 kg, magnesium chloride hydrate 0.178 kg, and sodium lactate (70%) 0.140 kg were mixed under heating, followed by granulation after addition of water 0.178 kg to form granules, and the granules were dried at 130° C. to obtain an electrolyte composition. Further, separately, glacial acetic acid 0.105 kg and anhydrous sodium acetate 0.144 kg were mixed to give an acetic acid/sodium acetate mixture. The above electrolyte composition 238.3 g, the acetic acid/sodium acetate mixture 9.95 g, and glucose 52.5 g were mixed with stirring to obtain a solid dialysis agent A. The molar ratio of acetic acid:sodium acetate in the solid dialysis agent A obtained is 1:1.

Example 18

First, sodium chloride 11.10 kg, potassium chloride 0.261 kg, calcium chloride hydrate 0.386 kg, magnesium chloride hydrate 0.178 kg, and anhydrous sodium acetate 0.072 kg were mixed under heating, followed by granulation after addition of water 0.178 kg to form granules, and the granules were dried at 130° C. to obtain an electrolyte composition. Further, separately, glacial acetic acid 0.105 kg and anhydrous sodium acetate 0.144 kg were mixed to give an acetic acid/sodium acetate mixture. The above electrolyte composition 239.9 g, the acetic acid/sodium acetate mixture 4.97 g, anhydrous citric acid 2.24 g, and glucose 52.5 g were mixed with stirring to obtain a solid dialysis agent A. The molar ratio of acetic acid:sodium acetate in the solid dialysis agent A obtained is 1:1.5.

(2) Measurement of Volatilized Acetic Acid Concentration and 5-HMF Amount of 35-Fold Concentrated Agent A Solution after Storage Each solid dialysis agent A in a predetermined amount shown in Table 14 was accommodated in a polyethylene bag. Further, this was accommodated in a packaging bag shown in Table 13, sealed, and stored at 25° C. for two months.

TABLE 13

| Notation of packaging bag | Composition of packaging bag |
|---|---|
| PET/AL/PE bag | A laminated bag (water vapor transmission is substantially 0 g/m² · 24 hr) made of a laminate wherein a polyethylene terephthalate film, an aluminum foil, and a polyethylene film are laminated. |
| PET/Si-PET/PE bag | A laminated bag (water vapor transmission is 0.2 g/m² · 24 hr) made of a laminate wherein a polyethylene terephthalate film, a silicon dioxide vapor deposited polyethylene terephthalate film, and a polyethylene film are laminated. |
| PET/AL/PE bag + zeolite (1%) | The PET/AL/PE bag in which 1 part by weight of zeolite is added as a desiccant, per 100 parts by weight of the solid dialysis agent A to be accommodated therein. |
| PET/AL/PE bag + zeolite (5%) | The PET/AL/PE bag in which 5 part by weight of zeolite is added as a desiccant, per 100 parts by weight of the solid dialysis agent A to be accommodated therein. |
| PET/AL/PE bag + anhydrous magnesium sulfate (5%) | The PET/AL/PE bag in which 5 parts by weight of anhydrous magnesium sulfate are added as a desiccant, per 100 parts by weight of the solid dialysis agent A to be accommodated therein. |

Before storage, after one month storage, and after two months storage, a gas detector tube was set in a polyethylene bag so that a fixed amount of a sample gas was passed through the detector tube for the measurement of acetic acid, and the volatilized acetic acid concentration was measured by using a gas detector tube type gas measuring instrument (manufacturer: GASTEC, model number: GV-100S).

Further, before storage, after one month storage, and after two months storage, a 35-fold concentrated agent A solution was obtained by dissolving a predetermined amount shown in Table 14 of each solid dialysis agent A in purified water to a volume of 500 mL that was concentrated to 35 times the concentration of each component in the finally prepared dialysate. The 5-HMF content of the 35-fold concentrated agent A solution obtained was measured in the same manner as in the above Test Example 1. In addition, as for the 35-fold concentrated agent A solution that was prepared using a solid dialysis agent A after the preparation, the pH was measured in the same manner as in the above Test Example 1.

TABLE 14

| Solid dialysis agent A used | Amount (g) of solid dialysis agent A accommodated in packaging bag and amount (g) of solid dialysis agent A dissolved in purified water |
|---|---|
| Example 8 | 149.5 |
| Example 9 | 149.7 |

TABLE 14-continued

| Solid dialysis agent A used | Amount (g) of solid dialysis agent A accommodated in packaging bag and amount (g) of solid dialysis agent A dissolved in purified water |
|---|---|
| Example 10 | 149.9 |
| Example 11 | 150.1 |
| Example 12 | 150.3 |
| Example 13 | 150.5 |
| Example 14 | 150.8 |
| Example 15 | 153.6 |
| Example 16 | 154.1 |
| Example 17 | 150.4 |
| Example 18 | 149.8 |
| Comparative Example 7 | 149.1 |

The results of measuring the pH of the 35-fold concentrated agent A solution prepared by using the solid dialysis agent A before storage were shown in Table 15, the results of measuring the volatilized acetic acid concentration of the solid dialysis agent A before and after storage are shown in Table 16, and the results of measuring the 5-HMF content in the 35-fold concentrated agent A solution prepared by using the solid dialysis agent A before and after storage are shown in Table 17.

As a result, in the solid dialysis agent A of Comparative Example 7 before storage, the volatilized acetic acid concentration and the 5-HMF content were high, indicating that it was not able to suppress the volatilization of acetic acid and the degradation of glucose. Further, in the solid dialysis agent A of Comparative Example 7 after one month and two months storage in a PET/AL/PE bag, since the generation of hydrogen chloride gas was also observed, the volatilized hydrogen chloride concentration was measured by using a detector tube for hydrogen chloride measurement in the same manner as in the measurement of the volatilized acetic acid concentration, and it was revealed that the hydrogen chloride gas was generated in 100 ppm after one month storage and in 80 ppm after two months storage. Meanwhile, in the solid dialysis agent A of each of Examples 9 to 18, even two months after storage, the volatilization of acetic acid and the degradation of glucose could be sufficiently suppressed. Further, from the present test results, it was revealed that the volatilization of acetic acid and the degradation of glucose could be suppressed more effectively by adding a desiccant to a packaging body storing the solid dialysis agent A.

TABLE 15

| Solid dialysis agent A used | Molar ratio of acetic acid and sodium acetate | pH of liquid dialysis agent A |
|---|---|---|
| Example 8 | 1:0.5 | 4.03 |
| Example 9 | 1:0.75 | 4.19 |
| Example 10 | 1:1 | 4.33 |
| Example 11 | 1:1.25 | 4.41 |
| Example 12 | 1:1.5 | 4.51 |
| Example 13 | 1:1.75 | 4.56 |
| Example 14 | 1:2 | 4.59 |
| Example 15 | 1:1 | 4.31 |
| Example 16 | 1:1.4 | 4.47 |
| Example 17 | 1:1 | 4.32 |
| Example 18 | 1:1.5 | 3.94 |
| Comparative Example 7 | 1:0 | 2.52 |

TABLE 16

Measurement results of volatilized acetic acid concentration (ppm)

| | Before storage | After one month storage PET/AL/PE bag | After two months storage | | | | |
|---|---|---|---|---|---|---|---|
| | | | PET/AL/PE bag | PET/AL/PE bag + zeolite (1%) | PET/AL/PE bag + zeolite (5%) | PET/AL/PE bag + anhydrous magnesium sulfate (5%) | PET/Si-PET/PE bag |
| Example 8 | 400 | Not measured | Not measured | Not measured | 300 | Not measured | Not measured |
| Example 9 | 250 | 400 | 550 | 525 | 100 | 180 | Not measured |
| Example 10 | 40 | 20 | 22 | 11 | 6 | 7 | 20 |
| Example 11 | 35 | 40 | 20 | 25 | 18 | 25 | 21 |
| Example 12 | 20 | 50 | 20 | 22 | 15 | 15 | Not measured |
| Example 13 | 30 | 50 | Not measured | Not measured | 7 | 40 | Not measured |
| Example 14 | 15 | 60 | 15 | Not measured | 10 | 10 | Not measured |
| Example 15 | 20 | 20 | 20 | Not measured | 8 | 5 | Not measured |
| Example 16 | 20 | 45 | 8 | Not measured | 8 | 8 | Not measured |
| Example 17 | 20 | 35 | 25 | Not measured | 7 | 10 | Not measured |
| Example 18 | 20 | 20 | 10 | Not measured | 10 | 10 | Not measured |
| Comparative Example 7 | 700 | >1000 | * Unmeasurable | Not measured | 800 | * Unmeasurable | Not measured |

The results of the solid dialysis agent A accommodated in "PET/AL/PE bag + zeolite (1%)" show the average value in the case of n = 2. In the table, the symbol * indicates that a laminated portion of the packaging bag caused a detachment by the generated gas. Because it was expected that such detachment was caused by the failure of maintaining sealing performances in the packaging bag, the measurement of the volatilized acetic acid concentration was defined as "unmeasurable". Note that the gas generated was confirmed to be hydrogen chloride gas.

TABLE 17

Measurement results of 5-HMF (absorbance: 284 nm)

|  | Before storage | After one month storage PET/AL/PE bag | After two months storage | | | | |
|---|---|---|---|---|---|---|---|
|  |  |  | PET/AL/PE bag | PET/AL/PE bag + zeolite (1%) | PET/AL/PE bag + zeolite (5%) | PET/AL/PE bag + anhydrous magnesium sulfate (5%) | PET/Si-PET/PE bag |
| Example 8 | 0.0043 | Not measured | Not measured | Not measured | 0.0328 | Not measured | Not measured |
| Example 9 | 0.0036 | 0.0048 | 0.0063 | 0.0104 | 0.0041 | 0.0041 | Not measured |
| Example 10 | 0.0062 | 0.0089 | 0.0071 | 0.0049 | 0.0069 | 0.0067 | 0.0063 |
| Example 11 | 0.0053 | 0.0063 | 0.0061 | 0.0041 | 0.0056 | 0.0054 | 0.0051 |
| Example 12 | 0.0049 | 0.0054 | 0.0048 | 0.0046 | 0.0043 | 0.0043 | Not measured |
| Example 13 | 0.0042 | 0.0054 | Not measured | Not measured | 0.0039 | 0.0041 | Not measured |
| Example 14 | 0.0033 | 0.0046 | 0.0037 | Not measured | 0.0036 | 0.0035 | Not measured |
| Example 15 | 0.0032 | 0.0035 | 0.0025 | Not measured | 0.0025 | 0.0023 | Not measured |
| Example 16 | 0.0050 | 0.0053 | 0.0044 | Not measured | 0.0044 | 0.0042 | Not measured |
| Example 17 | 0.0088 | 0.0087 | 0.0083 | Not measured | 0.0078 | 0.0077 | Not measured |
| Example 18 | 0.0071 | 0.0074 | 0.0061 | Not measured | 0.0064 | 0.0066 | Not measured |
| Comparative Example 7 | 0.0056 | 0.0330 | 0.0705 | Not measured | 0.0342 | 0.0516 | Not measured |

The results of the solid dialysis agent A accommodated in the "PET/AL/PE bag + zeolite (1%)" show the average value in the case of n = 2.

Test Example 7

(1) Preparation of Solid Dialysis Agent A

Example 19

First, sodium chloride 10.99 kg, potassium chloride 0.261 kg, calcium chloride hydrate 0.386 kg, magnesium chloride hydrate 0.178 kg, and anhydrous sodium acetate 0.072 kg were mixed under heating, and granulated after addition of water 0.178 kg, thereby to form granules. After that, when these granules were dried at 130° C., an electrolyte composition having different moisture content was obtained by changing the drying time. In addition, separately, glacial acetic acid 0.105 kg and anhydrous sodium acetate 0.144 kg were mixed. The electrolyte composition 237.8 g, the acetic acid/sodium acetate mixture 9.95 g, and glucose 52.5 g were mixed with stirring to obtain a solid dialysis agent A. The moisture contents of the solid dialysis agents A obtained from this procedure were 0.8% by weight (Example 19-1), 1.0% by weight (Example 19-2), 1.1% by weight (Example 19-3), 1.2% by weight (Example 19-4), respectively. Further, the molar ratio of acetic acid:sodium acetate in the solid dialysis agent A obtained is 1:1.25.

(2) Evaluation of Solid Dialysis Agent A

For each solid dialysis agent A obtained above, the volatilized acetic acid concentration was measured in the same manner as in the above Test Example 5.

The results obtained are shown in Table 18. As can clearly be seen from Table 18, when the moisture content of the solid dialysis agent A is 1.0% by weight or less, the solid dialysis agent A showed a significantly lower value of 30 ppm or less of the volatilized acetic acid concentration, and a particularly remarkable effect of reducing the acetic acid odor was observed.

TABLE 18

|  | Moisture content (% by weight) | Volatilized acetic acid concentration (ppm) |
|---|---|---|
| Example 19-1 | 0.8 | 15 |
| Example 19-2 | 1.0 | 30 |
| Example 19-3 | 1.1 | 400 |
| Example 19-4 | 1.2 | 400 |

Test Example 8

(1) Preparation of Mixture of Acetic Acid/Sodium Acetate

Sodium acetate was dried thoroughly at 130° C. to obtain anhydrous sodium acetate having a moisture content of 0.27% by weight. Then, moisture in glacial acetic acid was removed by using molecular sieves (manufacturer: Wako Pure Chemical Industries; model number: 133-08645), and purified water was added to the glacial acetic acid so as to have moisture contents of 1.05% by weight, 1.52% by weight, 2.00% by weight, 2.23% by weight, 2.47% by weight, and 2.94% by weight, respectively. Each acetic acid 0.300 kg prepared in this way and anhydrous sodium acetate 0.410 kg were mixed to obtain an acetic acid/sodium acetate mixture. The moisture contents of the resulting mixtures were 0.6% by weight, 0.8% by weight, 1.0% by weight, 1.1% by weight, 1.2% by weight, and 1.4% by weight. In the present test, the moisture contents were all measured by using a Karl Fischer moisture meter (manufacturer: Hiranuma Sangyo Corp.; model number: AVQ-6).

(2) Evaluation of Mixture of Acetic Acid/Sodium Acetate

For each mixture obtained above, the volatilized acetic acid concentration was measured in the same manner as in the above Test Example 5.

The results obtained are shown in Table 19. As a result, when the moisture content of the acetic acid/sodium acetate mixture is 1.0% by weight or less, particularly 0.8% by weight or less, the volatilized acetic acid concentration becomes a remarkably low value of 30 ppm or less, by which it was confirmed that the acetic acid odor was particularly remarkably reduced.

TABLE 19

| | Moisture content (% by weight) of acetic acid/sodium acetate mixture | | | | | |
|---|---|---|---|---|---|---|
| | 0.6 | 0.8 | 1.0 | 1.1 | 1.2 | 1.4 |
| Volatilized acetic acid concentration (ppm) | 30 | 30 | 80 | 180 | 200 | 400 |

What is claimed is:

1. A dialysis agent A comprising a mixture containing glucose, acetic acid, and acetate salt, but not sodium bicarbonate,
wherein the molar ratio of acetic acid: acetate salt is 1:0.5 to 1:2, and
wherein a total amount of the acetic acid and acetate salt contained in the dialysis agent A is between 2mEq/L and 6mEq/L when the dialysis agent A is dissolved in 1 L of a bicarbonate dialysate.

2. The dialysis agent A according to claim 1, wherein when the dialysis agent A is converted into a state of an aqueous solution that is concentrated to 35 times the concentration of each component in the finally prepared dialysate, the pH is 3.9 to 4.6.

3. The dialysis agent A according to claim 1, wherein the acetate salt is sodium acetate.

4. The dialysis agent A according to claim 1, further comprising a physiologically available electrolyte other than acetic acid and acetate salt, and wherein the physiologically available electrolyte other than acetic acid and acetate salt is not sodium bicarbonate.

5. The dialysis agent A according to claim 4, wherein the electrolyte comprises sodium chloride, potassium chloride, magnesium chloride, and calcium chloride.

6. The dialysis agent A according to claim 1, which is in the form of a solid.

7. The dialysis agent A according to claim 6, wherein the acetic acid and acetate salt are contained as a mixture of acetic acid and acetate salt.

8. The dialysis agent A according to claim 6, wherein the acetic acid and acetate salt are contained as a mixture of glacial acetic acid and anhydrous sodium acetate.

9. The dialysis agent A according to claim 1, comprising a first granular material consisting of a mixture of the acetic acid and the acetate salt and a second granular material comprising a physiologically available electrolyte other than the acetic acid and the acetate salt, wherein the physiologically available electrolyte other than the acetic acid and the acetate salt is not sodium bicarbonate, wherein all of the acetate salt in the dialysis agent A is contained in the first granular material, or some of the acetate salt in the dialysis agent A is also contained in the second granular material, and wherein the glucose is contained in the second granular material, and/or the glucose is contained in a third granular material separate from the first granular material and the second granular material.

10. The dialysis agent A according to claim 9, wherein the second material comprises sodium chloride, potassium chloride, magnesium chloride, and calcium chloride as an electrolyte.

11. The dialysis agent A according to claim 9, wherein the second material further comprises as an electrolyte one or more organic acid salt(s) other than acetate salt.

12. The dialysis agent A according to claim 11, wherein the one or more organic acid salt(s) is/are selected from the group consisting of sodium lactate, sodium gluconate, sodium citrate, sodium malate, and sodium succinate.

13. The dialysis agent A according to claim 1, comprising a moisture content of 1.0% by weight or less.

14. The dialysis agent A according to claim 1, which is accommodated in a packaging container having a water vapor transmission of 0.5 g/m2·24 h or less.

15. The dialysis agent A according to claim 1, which is accommodated in a packaging container together with a desiccant.

16. A two pack type dialysis agent comprising the dialysis agent A according to claim 1 and a dialysis agent B containing sodium hydrogen carbonate.

17. A method for preparing a bicarbonate dialysate, comprising the step of mixing the dialysis agent A according to claim 1 and a dialysis agent B containing sodium hydrogen carbonate with water in an amount so as to have the total acetate ions of between 2 mEq/L or more and less than 6 mEq/L.

* * * * *